US011345753B2

(12) United States Patent
Cao et al.

(10) Patent No.: US 11,345,753 B2
(45) Date of Patent: May 31, 2022

(54) TIM-3 ANTIBODY, ANTIGEN BINDING FRAGMENT THEREOF, AND MEDICINAL USES THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Zhuoxiao Cao, Shanghai (CN); Yayuan Fu, Shanghai (CN); Ting Zhang, Shanghai (CN); Weikang Tao, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 171 days.

(21) Appl. No.: 16/487,321

(22) PCT Filed: Feb. 26, 2018

(86) PCT No.: PCT/CN2018/077190
§ 371 (c)(1),
(2) Date: Aug. 20, 2019

(87) PCT Pub. No.: WO2018/153366
PCT Pub. Date: Aug. 30, 2018

(65) Prior Publication Data
US 2019/0375839 A1 Dec. 12, 2019

(30) Foreign Application Priority Data
Feb. 27, 2017 (CN) ......................... 201710108747.2

(51) Int. Cl.
*A61K 39/395* (2006.01)
*A61K 39/00* (2006.01)
*C07K 16/00* (2006.01)
*C07K 16/46* (2006.01)
*C07H 21/04* (2006.01)
*C07K 16/28* (2006.01)
*G01N 33/68* (2006.01)

(52) U.S. Cl.
CPC ......... *C07K 16/2803* (2013.01); *G01N 33/68* (2013.01); *A61K 2039/505* (2013.01); *C07K 2317/24* (2013.01); *C07K 2317/52* (2013.01); *C07K 2317/567* (2013.01); *C07K 2317/92* (2013.01); *G01N 2333/705* (2013.01)

(58) Field of Classification Search
None
See application file for complete search history.

(56) References Cited

U.S. PATENT DOCUMENTS

2015/0218274 A1* 8/2015 Sabatos-Peyton ...... A61P 35/00
424/136.1

FOREIGN PATENT DOCUMENTS

| | | | |
|---|---|---|---|
| CN | 102492038 | A | 6/2012 |
| CN | 103079644 | A | 5/2013 |
| CN | 106132991 | A | 11/2016 |
| WO | 2011159877 | A2 | 12/2011 |
| WO | 2013006490 | A2 | 1/2013 |
| WO | 2015117002 | A1 | 8/2015 |
| WO | 2016144803 | A2 | 9/2016 |
| WO | 2016161270 | A1 | 10/2016 |

OTHER PUBLICATIONS

Campo et al. Zinc inhibits the Mixed Lymphocyte Culture. Biological Trace Element Research vol. 79, pp. 15-22 (2001) (Year: 2001).*

Stites et al.Basic and Clinical Immunlogy, 8th edition, pp. 30-31, 208-209, 246-247, 1994 (Year: 1994).*

Reinsmoen et al. Evaluation of the Cellular Immune Response in Transplantation. In Manual of Clinical Laboratory Immunology, 6th Edition, by Rose, N.R., pp. 1164-1175, 1994. (Year: 1994).*

Piccotti et al. INTERLEUKIN-12 (IL-12)-Driven Alloimmune Responses In Vitro and In Vivo. Transplantation: Jun. 15, 1999—vol. 67—Issue 11—p. 1453-1460. (Year: 1999).*

Kahan BD., Immunosuppressive therapy. Curr Opin Immunol. Oct. 1992;4(5):553-60. (Year: 1992).*

Rezazadeh et al. Blockade of PD-1 and TIM-3 immune checkpoints fails to restore the function of exhausted CD8+ T cells in early clinical stages of chronic lymphocytic leukemia. Immunologic Research (2020) 68:269-279. (Year: 2020).*

Monney L, Sabatos CA, Gaglia JL, et al. Th1-specific cell surface protein Tim-3 regulates macrophage activation and severity of an autoimmune disease. Nature. 2002;415:536-541. (Year: 2002).*

Kikushige, Y. et al., “TIM-3 as a novel therapeutic target for eradicating acute myelogenous leukemia stem cells,” Int J Hematol, vol. 98, pp. 627-633 (2013).

Clayton et al, “T Cell Ig and Mucin Domain-Containing Protein 3 Is Recruited to the Immune Synapse, Disrupts Stable Synapse Formation, and Associates with Receptor Phosphatases,” The Journal of Immunology, vol. 192, No. 2, pp. 782-791 (2014).

Jones et al, “TIM-3 expression defines a novel population of dysfunctional T cells with highly elevated frequencies in progressive HIV-1 infection,” Journal of Experimental Medicine, vol. 205, No. 12, pp. 2763-2779 (Dec. 2008).

(Continued)

*Primary Examiner* — Maher M Haddad
(74) *Attorney, Agent, or Firm* — Ice Miller LLP

(57) ABSTRACT

A TIM-3 antibody, an antigen-binding fragment thereof, and medical uses thereof are described. More specifically, the present invention provides a rat-derived antibody containing a CDR region of the TIM-3 antibody, a chimeric antibody or a human-derived antibody thereof, and a pharmaceutical composition containing the TIM-3 antibody and the antigen-binding fragment thereof, as well as uses thereof serving as a drug. In particular, the present invention provides uses of a human-derived TIM-3 antibody in the preparation of drugs for treating TIM-3-related conditions.

18 Claims, 4 Drawing Sheets

Figure 1:
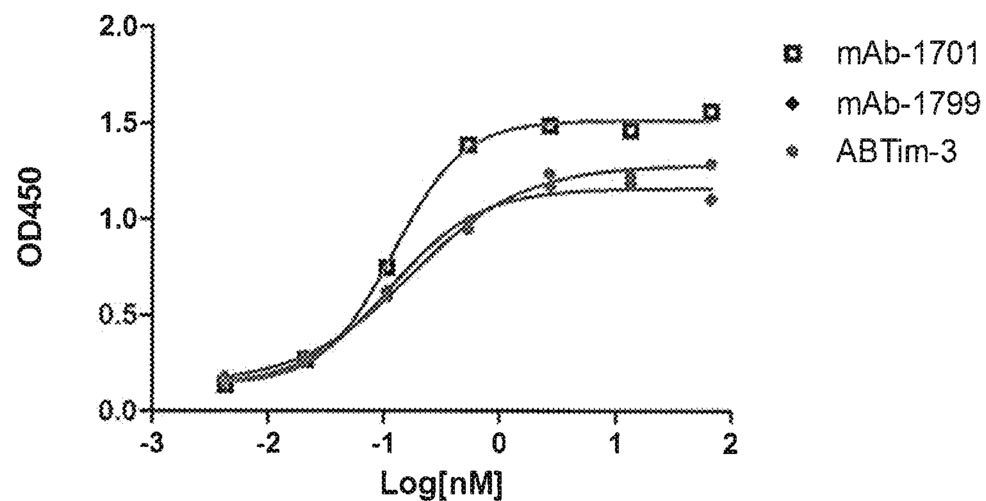

Specification includes a Sequence Listing.

(56) References Cited

OTHER PUBLICATIONS

Ngiow et al, "Anti-TIM3 Antibody Promotes T Cell IFN-Gamma-Mediated Antitumor Immunity and Suppresses Established Tumors," Cancer Research, vol. 71, No. 21, pp. 1-5 (May 2011).
Guo et al, "Combined TIM-3 blockade and CD137 activation affords the long-term protection in a murine model of ovarian cancer," Journal of Translational Medicine, vol. 11, p. 215 (2013).
Ngiow et al, "Prospects for TIM3-Targeted Antitumor Immunotherapy," Cancer Research, vol. 71, No. 21, pp. 6567-6571 (Nov. 2011).
Int'l Search Report dated May 29, 2018 in Int'l Application No. PCT/CN2018/077190.

* cited by examiner

SEQUENCE LISTING

```
<160> NUMBER OF SEQ ID NOS: 72

<210> SEQ ID NO 1
<211> LENGTH: 430
<212> TYPE: PRT
<213> ORGANISM: Artificial sequence
<220> FEATURE:
<223> OTHER INFORMATION: Fusion protein of TIM-3 extracellular region
      and hIgG1 Fc

<400> SEQUENCE: 1

Met Glu Phe Gly Leu Ser Trp Leu Phe Leu Val Ala Ile Leu Lys Gly
1               5                   10                  15

Val Gln Cys Ser Glu Val Glu Tyr Arg Ala Glu Val Gly Gln Asn Ala
            20                  25                  30

Tyr Leu Pro Cys Phe Tyr Thr Pro Ala Ala Pro Gly Asn Leu Val Pro
        35                  40                  45

Val Cys Trp Gly Lys Gly Ala Cys Pro Val Phe Glu Cys Gly Asn Val
    50                  55                  60
```

```
Val Leu Arg Thr Asp Glu Arg Asp Val Asn Tyr Trp Thr Ser Arg Tyr
65                  70                  75                  80

Trp Leu Asn Gly Asp Phe Arg Lys Gly Asp Val Ser Leu Thr Ile Glu
                85                  90                  95

Asn Val Thr Leu Ala Asp Ser Gly Ile Tyr Cys Cys Arg Ile Gln Ile
            100                 105                 110

Pro Gly Ile Met Asn Asp Glu Lys Phe Asn Leu Lys Leu Val Ile Lys
        115                 120                 125

Pro Ala Lys Val Thr Pro Ala Pro Thr Arg Gln Arg Asp Phe Thr Ala
    130                 135                 140

Ala Phe Pro Arg Met Leu Thr Thr Arg Gly His Gly Pro Ala Glu Thr
145                 150                 155                 160

Gln Thr Leu Gly Ser Leu Pro Asp Ile Asn Leu Thr Gln Ile Ser Thr
                165                 170                 175

Leu Ala Asn Glu Leu Arg Asp Ser Arg Leu Ala Asn Asp Leu Arg Asp
            180                 185                 190

Ser Gly Ala Thr Ile Arg Glu Pro Lys Ser Ser Asp Lys Thr His Thr
        195                 200                 205

Cys Pro Pro Cys Pro Ala Pro Glu Leu Leu Gly Gly Pro Ser Val Phe
    210                 215                 220

Leu Phe Pro Pro Lys Pro Lys Asp Thr Leu Met Ile Ser Arg Thr Pro
225                 230                 235                 240

Glu Val Thr Cys Val Val Val Asp Val Ser His Glu Asp Pro Glu Val
                245                 250                 255

Lys Phe Asn Trp Tyr Val Asp Gly Val Glu Val His Asn Ala Lys Thr
            260                 265                 270

Lys Pro Arg Glu Glu Gln Tyr Asn Ser Thr Tyr Arg Val Val Ser Val
        275                 280                 285

Leu Thr Val Leu His Gln Asp Trp Leu Asn Gly Lys Glu Tyr Lys Cys
    290                 295                 300

Lys Val Ser Asn Lys Ala Leu Pro Ala Pro Ile Glu Lys Thr Ile Ser
305                 310                 315                 320

Lys Ala Lys Gly Gln Pro Arg Glu Pro Gln Val Tyr Thr Leu Pro Pro
                325                 330                 335

Ser Arg Asp Glu Leu Thr Lys Asn Gln Val Ser Leu Thr Cys Leu Val
            340                 345                 350

Lys Gly Phe Tyr Pro Ser Asp Ile Ala Val Glu Trp Glu Ser Asn Gly
        355                 360                 365

Gln Pro Glu Asn Asn Tyr Lys Thr Thr Pro Pro Val Leu Asp Ser Asp
    370                 375                 380

Gly Ser Phe Phe Leu Tyr Ser Lys Leu Thr Val Asp Lys Ser Arg Trp
385                 390                 395                 400

Gln Gln Gly Asn Val Phe Ser Cys Ser Val Met His Glu Ala Leu His
                405                 410                 415

Asn His Tyr Thr Gln Lys Ser Leu Ser Leu Ser Pro Gly Lys
            420                 425                 430
```

<210> SEQ ID NO 2
<211> LENGTH: 215
<212> TYPE: PRT
<213> ORGANISM: Artificial sequence
<220> FEATURE:
<223> OTHER INFORMATION: Extracellular region of TIM-3 with Flag and His tag

```
<400> SEQUENCE: 2

Met Glu Phe Gly Leu Ser Trp Leu Phe Leu Val Ala Ile Leu Lys Gly
1               5                   10                  15

Val Gln Cys Ser Glu Val Glu Tyr Arg Ala Glu Val Gly Gln Asn Ala
            20                  25                  30

Tyr Leu Pro Cys Phe Tyr Thr Pro Ala Ala Pro Gly Asn Leu Val Pro
        35                  40                  45

Val Cys Trp Gly Lys Gly Ala Cys Pro Val Phe Glu Cys Gly Asn Val
    50                  55                  60

Val Leu Arg Thr Asp Glu Arg Asp Val Asn Tyr Trp Thr Ser Arg Tyr
65                  70                  75                  80

Trp Leu Asn Gly Asp Phe Arg Lys Gly Asp Val Ser Leu Thr Ile Glu
                85                  90                  95

Asn Val Thr Leu Ala Asp Ser Gly Ile Tyr Cys Cys Arg Ile Gln Ile
            100                 105                 110

Pro Gly Ile Met Asn Asp Glu Lys Phe Asn Leu Lys Leu Val Ile Lys
        115                 120                 125

Pro Ala Lys Val Thr Pro Ala Pro Thr Arg Gln Arg Asp Phe Thr Ala
    130                 135                 140

Ala Phe Pro Arg Met Leu Thr Thr Arg Gly His Gly Pro Ala Glu Thr
145                 150                 155                 160

Gln Thr Leu Gly Ser Leu Pro Asp Ile Asn Leu Thr Gln Ile Ser Thr
                165                 170                 175

Leu Ala Asn Glu Leu Arg Asp Ser Arg Leu Ala Asn Asp Leu Arg Asp
            180                 185                 190

Ser Gly Ala Thr Ile Arg Gly Ser Ser Asp Tyr Lys Asp Asp Asp Asp
        195                 200                 205

Lys His His His His His His
    210                 215


<210> SEQ ID NO 3
<211> LENGTH: 301
<212> TYPE: PRT
<213> ORGANISM: Artificial sequence
<220> FEATURE:
<223> OTHER INFORMATION: Full length of TIM-3

<400> SEQUENCE: 3

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
```

```
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300


<210> SEQ ID NO 4
<211> LENGTH: 121
<212> TYPE: PRT
<213> ORGANISM: Mus musculus

<400> SEQUENCE: 4

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Ala Asp Ile Ile Pro Asn Asn Gly Gly Ser Lys Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Ser Val Ser Ala
        115                 120


<210> SEQ ID NO 5
<211> LENGTH: 107
<212> TYPE: PRT
<213> ORGANISM: Mus musculus

<400> SEQUENCE: 5

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Pro Ile Gly Ile Trp
            20                  25                  30

Leu Ala Trp Tyr Gln Gln Lys Pro Gly Lys Ser Pro Gln Leu Leu Ile
```

```
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Ser Pro Trp
                85                  90                  95

Thr Phe Gly Gly Gly Thr Lys Leu Glu Ile Lys
            100                 105


<210> SEQ ID NO 6
<211> LENGTH: 122
<212> TYPE: PRT
<213> ORGANISM: Mus musculus

<400> SEQUENCE: 6

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
        35                  40                  45

Ala Asn Ile Asn Tyr Asp Gly Ser Ser Thr Tyr Tyr Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Asn Ser Leu Lys Ser Asp Asp Thr Ala Thr Tyr Tyr Cys
                85                  90                  95

Ala Arg Asp Val Gly Tyr Tyr Gly Gly Asn Tyr Gly Phe Ala Tyr Trp
            100                 105                 110

Gly Gln Gly Thr Leu Val Thr Val Ser Ala
        115                 120


<210> SEQ ID NO 7
<211> LENGTH: 107
<212> TYPE: PRT
<213> ORGANISM: Mus musculus

<400> SEQUENCE: 7

Asp Ile Gln Met Thr Gln Ser Pro Ala Ser Leu Ser Ala Ser Val Gly
1               5                   10                  15

Glu Thr Val Thr Ile Thr Cys Arg Ala Ser Asp Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln Gln His Tyr Gly Ser Pro Leu
                85                  90                  95

Thr Phe Gly Ala Gly Thr Lys Leu Glu Leu Lys
            100                 105


<210> SEQ ID NO 8
<211> LENGTH: 5
<212> TYPE: PRT
```

<213> ORGANISM: Mus musculus

<400> SEQUENCE: 8

Asp Tyr Tyr Met Asn
1               5

<210> SEQ ID NO 9
<211> LENGTH: 17
<212> TYPE: PRT
<213> ORGANISM: Mus musculus

<400> SEQUENCE: 9

Asp Ile Ile Pro Asn Asn Gly Gly Ser Lys Tyr Asn Gln Lys Phe Lys
1               5                   10                  15

Asp

<210> SEQ ID NO 10
<211> LENGTH: 12
<212> TYPE: PRT
<213> ORGANISM: Mus musculus

<400> SEQUENCE: 10

Trp Gly Tyr Gly Ser Ser Tyr Arg Trp Phe Asp Tyr
1               5                   10

<210> SEQ ID NO 11
<211> LENGTH: 11
<212> TYPE: PRT
<213> ORGANISM: Mus musculus

<400> SEQUENCE: 11

Leu Ala Ser Gln Pro Ile Gly Ile Trp Leu Ala
1               5                   10

<210> SEQ ID NO 12
<211> LENGTH: 7
<212> TYPE: PRT
<213> ORGANISM: Mus musculus

<400> SEQUENCE: 12

Ala Ala Thr Ser Leu Ala Asp
1               5

<210> SEQ ID NO 13
<211> LENGTH: 9
<212> TYPE: PRT
<213> ORGANISM: Mus musculus

<400> SEQUENCE: 13

Gln Gln Leu Tyr Ser Ser Pro Trp Thr
1               5

<210> SEQ ID NO 14
<211> LENGTH: 5
<212> TYPE: PRT
<213> ORGANISM: Mus musculus

<400> SEQUENCE: 14

Asp Tyr Tyr Met Ala
1               5

<210> SEQ ID NO 15
<211> LENGTH: 17
<212> TYPE: PRT

<213> ORGANISM: Mus musculus

<400> SEQUENCE: 15

```
Asn Ile Asn Tyr Asp Gly Ser Ser Thr Tyr Tyr Leu Asp Ser Leu Lys
1               5                   10                  15

Ser
```

<210> SEQ ID NO 16
<211> LENGTH: 13
<212> TYPE: PRT
<213> ORGANISM: Mus musculus

<400> SEQUENCE: 16

```
Asp Val Gly Tyr Tyr Gly Gly Asn Tyr Gly Phe Ala Tyr
1               5                   10
```

<210> SEQ ID NO 17
<211> LENGTH: 11
<212> TYPE: PRT
<213> ORGANISM: Mus musculus

<400> SEQUENCE: 17

```
Arg Ala Ser Asp Asn Ile Tyr Ser Tyr Leu Ala
1               5                   10
```

<210> SEQ ID NO 18
<211> LENGTH: 7
<212> TYPE: PRT
<213> ORGANISM: Mus musculus

<400> SEQUENCE: 18

```
Asn Ala Lys Thr Leu Ala Glu
1               5
```

<210> SEQ ID NO 19
<211> LENGTH: 9
<212> TYPE: PRT
<213> ORGANISM: Mus musculus

<400> SEQUENCE: 19

```
Gln Gln His Tyr Gly Ser Pro Leu Thr
1               5
```

<210> SEQ ID NO 20
<211> LENGTH: 121
<212> TYPE: PRT
<213> ORGANISM: Artificial sequence
<220> FEATURE:
<223> OTHER INFORMATION: h1701 heavy chain variable region

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn Asn Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
```

```
                85                  90                  95

Ala Arg Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 21
<211> LENGTH: 107
<212> TYPE: PRT
<213> ORGANISM: Artificial sequence
<220> FEATURE:
<223> OTHER INFORMATION: h1701 light chain variable region

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Pro Ile Gly Ile Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Tyr Ser Ser Pro Trp
                85                  90                  95

Thr Phe Gly Gly Gly Thr Lys Val Glu Ile Lys
            100                 105


<210> SEQ ID NO 22
<211> LENGTH: 121
<212> TYPE: PRT
<213> ORGANISM: Artificial sequence
<220> FEATURE:
<223> OTHER INFORMATION: humanized heavy chain variable region after
      back-mutation, h1701-005/h1701-006

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn Asn Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 23
<211> LENGTH: 121
<212> TYPE: PRT
<213> ORGANISM: Artificial sequence
```

<220> FEATURE:
<223> OTHER INFORMATION: humanized light chain variable region after back-mutation,h1701-007/h1701-008

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Ile Pro Asn Asn Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Gly Tyr Gly Ser Ser Tyr Arg Trp Phe Asp Tyr Trp Gly
            100                 105                 110

Gln Gly Thr Leu Val Thr Val Ser Ser
        115                 120
```

<210> SEQ ID NO 24
<211> LENGTH: 121
<212> TYPE: PRT
<213> ORGANISM: Artificial sequence
<220> FEATURE:
<223> OTHER INFORMATION: humanized heavy chain variable region after back-mutation,h1701-009/h1701-010

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn Asn Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120
```

<210> SEQ ID NO 25
<211> LENGTH: 121
<212> TYPE: PRT
<213> ORGANISM: Artificial sequence
<220> FEATURE:
<223> OTHER INFORMATION: humanized heavy chain variable region after back-mutation,h1701-011/h1701-012

<400> SEQUENCE: 25

```
Gln Val Gln Leu Val Gln Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Ile Pro Asn Asn Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 26
<211> LENGTH: 121
<212> TYPE: PRT
<213> ORGANISM: Artificial sequence
<220> FEATURE:
<223> OTHER INFORMATION: humanized heavy chain variable region after
      back-mutation,h1701-013/h1701-014

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Lys Gln Ala Pro Gly Gln Gly Leu Glu Trp Ile
        35                  40                  45

Gly Asp Ile Ile Pro Asn Asn Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 27
<211> LENGTH: 121
<212> TYPE: PRT
<213> ORGANISM: Artificial sequence
<220> FEATURE:
<223> OTHER INFORMATION: humanized heavy chain variable region after
      back-mutation,h1701-015/h1701-016

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Ala Asp Ile Ile Pro Asn Asn Gly Gly Ser Lys Tyr Asn Gln Lys Phe
    50                  55                  60
```

```
Lys Asp Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 28
<211> LENGTH: 121
<212> TYPE: PRT
<213> ORGANISM: Artificial sequence
<220> FEATURE:
<223> OTHER INFORMATION: humanized heavy chain variable region after
      back-mutation,h1701-017/h1701-018

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Lys Gln Ala Pro Gly Gln Gly Leu Glu Trp Ile
        35                  40                  45

Ala Asp Ile Ile Pro Asn Asn Gly Gly Ser Lys Tyr Asn Gln Lys Phe
    50                  55                  60

Lys Asp Arg Ala Thr Leu Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 29
<211> LENGTH: 107
<212> TYPE: PRT
<213> ORGANISM: Artificial sequence
<220> FEATURE:
<223> OTHER INFORMATION: humanized light chain variable region after
      back-mutation,h1701-005/h1701-007/h1701-009/h1701-011/h1701-
      013/h1701-015/h1701-017

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Pro Ile Gly Ile Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Tyr Ser Ser Pro Trp
                85                  90                  95

Thr Phe Gly Gly Gly Thr Lys Val Glu Ile Lys
            100                 105
```

<210> SEQ ID NO 30
<211> LENGTH: 107
<212> TYPE: PRT
<213> ORGANISM: Artificial sequence
<220> FEATURE:
<223> OTHER INFORMATION: humanized light chain variable region after back-mutation,h1701-006/h1701-008/h1701-010/h1701-012/h1701-014/h1701-016/h1701-018

<400> SEQUENCE: 30

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Pro Ile Gly Ile Trp
            20                  25                  30

Leu Ala Trp Tyr Gln Gln Lys Pro Gly Lys Ser Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Tyr Ser Ser Pro Trp
                85                  90                  95

Thr Phe Gly Gly Gly Thr Lys Val Glu Ile Lys
            100                 105
```

<210> SEQ ID NO 31
<211> LENGTH: 122
<212> TYPE: PRT
<213> ORGANISM: Artificial sequence
<220> FEATURE:
<223> OTHER INFORMATION: h1799 heavy chain variable region

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Tyr Asp Gly Ser Ser Thr Tyr Tyr Leu Asp Ser Leu
    50                  55                  60

Lys Ser Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Tyr Tyr Gly Gly Asn Tyr Gly Phe Ala Tyr Trp
            100                 105                 110

Gly Gln Gly Thr Leu Val Thr Val Ser Ser
        115                 120
```

<210> SEQ ID NO 32
<211> LENGTH: 107
<212> TYPE: PRT
<213> ORGANISM: Artificial sequence
<220> FEATURE:
<223> OTHER INFORMATION: h1799 light chain variable region

<400> SEQUENCE: 32

```
Asp Ile Gln Met Thr Gln Ser Pro Ser Ser Leu Ser Ala Ser Val Gly
```

```
1               5                   10                  15

Asp Arg Val Thr Ile Thr Cys Arg Ala Ser Asp Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Ser Pro Leu
                85                  90                  95

Thr Phe Gly Gln Gly Thr Lys Leu Glu Ile Lys
            100                 105


<210> SEQ ID NO 33
<211> LENGTH: 122
<212> TYPE: PRT
<213> ORGANISM: Artificial sequence
<220> FEATURE:
<223> OTHER INFORMATION: humanized heavy chain variable region after
      back-mutation,h1799-005/h1799-006/h1799-007/h1799-008/h1799-009

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Tyr Asp Gly Ser Ser Thr Tyr Tyr Leu Asp Ser Leu
    50                  55                  60

Lys Ser Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Tyr Tyr Gly Gly Asn Tyr Gly Phe Ala Tyr Trp
            100                 105                 110

Gly Gln Gly Thr Leu Val Thr Val Ser Ser
        115                 120


<210> SEQ ID NO 34
<211> LENGTH: 122
<212> TYPE: PRT
<213> ORGANISM: Artificial sequence
<220> FEATURE:
<223> OTHER INFORMATION: humanized heavy chain variable region after
      back-mutation,h1799-010/h1799-011/h1799-012/h1799-013/h1799-014

<400> SEQUENCE: 34

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Tyr Asp Gly Ser Ser Thr Tyr Tyr Leu Asp Ser Leu
    50                  55                  60

Lys Ser Arg Phe Thr Ile Ser Arg Asp Asn Ala Lys Asn Ser Leu Tyr
```

```
65                  70                  75                  80

Leu Gln Met Asn Ser Leu Arg Ala Glu Asp Thr Ala Val Tyr Tyr Cys
                85                  90                  95

Ala Arg Asp Val Gly Tyr Tyr Gly Gly Asn Tyr Gly Phe Ala Tyr Trp
            100                 105                 110

Gly Gln Gly Thr Leu Val Thr Val Ser Ser
        115                 120


<210> SEQ ID NO 35
<211> LENGTH: 122
<212> TYPE: PRT
<213> ORGANISM: Artificial sequence
<220> FEATURE:
<223> OTHER INFORMATION: humanized heavy chain variable region after
      back-mutation,h1799-015/h1799-016/h1799-017/h1799-018/h1799-019

<400> SEQUENCE: 35

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Tyr Asp Gly Ser Ser Thr Tyr Tyr Leu Asp Ser Leu
    50                  55                  60

Lys Ser Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Asp Val Gly Tyr Tyr Gly Gly Asn Tyr Gly Phe Ala Tyr Trp
            100                 105                 110

Gly Gln Gly Thr Leu Val Thr Val Ser Ser
        115                 120


<210> SEQ ID NO 36
<211> LENGTH: 107
<212> TYPE: PRT
<213> ORGANISM: Artificial sequence
<220> FEATURE:
<223> OTHER INFORMATION: humanized light chain variable region after
      back-mutation,h1799-005/h1799-010/h1799-015

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Ser Pro Leu
                85                  90                  95

Thr Phe Gly Gln Gly Thr Lys Leu Glu Ile Lys
            100                 105
```

<210> SEQ ID NO 37
<211> LENGTH: 107
<212> TYPE: PRT
<213> ORGANISM: Artificial sequence
<220> FEATURE:
<223> OTHER INFORMATION: humanized light chain variable region after back-mutation, h1799-006/h1799-011/h1799-016

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Ser Pro Leu
                85                  90                  95

Thr Phe Gly Gln Gly Thr Lys Leu Glu Ile Lys
            100                 105
```

<210> SEQ ID NO 38
<211> LENGTH: 107
<212> TYPE: PRT
<213> ORGANISM: Artificial sequence
<220> FEATURE:
<223> OTHER INFORMATION: humanized light chain variable region after back-mutation,h1799-007/h1799-012/h1799-017

<400> SEQUENCE: 38

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Ile Tyr Ser Tyr
            20                  25                  30

Leu Ala Trp Tyr Gln Gln Lys Pro Gly Lys Ala Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Ser Pro Leu
                85                  90                  95

Thr Phe Gly Gln Gly Thr Lys Leu Glu Ile Lys
            100                 105
```

<210> SEQ ID NO 39
<211> LENGTH: 107
<212> TYPE: PRT
<213> ORGANISM: Artificial sequence
<220> FEATURE:
<223> OTHER INFORMATION: light chain variable region after back-mutation,h1799-008/h1799-013/h1799-018

<400> SEQUENCE: 39

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Ile Tyr Ser Tyr
            20                  25                  30
```

```
Leu Ala Trp Tyr Gln Gln Lys Pro Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Ser Pro Leu
                85                  90                  95

Thr Phe Gly Gln Gly Thr Lys Leu Glu Ile Lys
            100                 105


<210> SEQ ID NO 40
<211> LENGTH: 107
<212> TYPE: PRT
<213> ORGANISM: Artificial sequence
<220> FEATURE:
<223> OTHER INFORMATION: humanized light chain variable region after
      back-mutation,h1799-009/h1799-014/h1799-019

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Ile Tyr Ser Tyr
            20                  25                  30

Leu Ala Trp Tyr Gln Gln Lys Pro Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln His Tyr Gly Ser Pro Leu
                85                  90                  95

Thr Phe Gly Gln Gly Thr Lys Leu Glu Ile Lys
            100                 105


<210> SEQ ID NO 41
<211> LENGTH: 327
<212> TYPE: PRT
<213> ORGANISM: Artificial sequence
<220> FEATURE:
<223> OTHER INFORMATION: human IgG4 heavy chain constant region
      containing Fc mutation

<400> SEQUENCE: 41

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110
```

```
Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 42
<211> LENGTH: 107
<212> TYPE: PRT
<213> ORGANISM: Artificial sequence
<220> FEATURE:
<223> OTHER INFORMATION: human kappa light chain constant region

<400> SEQUENCE: 42

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 43
<211> LENGTH: 17
<212> TYPE: PRT
<213> ORGANISM: Artificial sequence
```

<220> FEATURE:
<223> OTHER INFORMATION: h1701 HCDR2
<220> FEATURE:
<221> NAME/KEY: misc_feature
<222> LOCATION: (5)..(5)
<223> OTHER INFORMATION: Xaa is Asn, Leu, Val, Met or Glu.
<220> FEATURE:
<221> NAME/KEY: misc_feature
<222> LOCATION: (6)..(6)
<223> OTHER INFORMATION: Xaa is Asn, Glu, Met, His, Lys, Leu, Ala or Val.
<220> FEATURE:
<221> NAME/KEY: misc_feature
<222> LOCATION: (7)..(7)
<223> OTHER INFORMATION: Xaa is Gly or Ala.

<400> SEQUENCE: 43

```
Asp Ile Ile Pro Xaa Xaa Xaa Gly Ser Lys Tyr Asn Gln Lys Phe Lys
1               5                   10                  15

Asp
```

<210> SEQ ID NO 44
<211> LENGTH: 121
<212> TYPE: PRT
<213> ORGANISM: Artificial sequence
<220> FEATURE:
<223> OTHER INFORMATION: h1701-005/h1701-006 heavy chain variable region CDR2 mutant
<220> FEATURE:
<221> NAME/KEY: misc_feature
<222> LOCATION: (54)..(54)
<223> OTHER INFORMATION: Xaa is Asn, Leu, Val, Met or Glu.
<220> FEATURE:
<221> NAME/KEY: misc_feature
<222> LOCATION: (55)..(55)
<223> OTHER INFORMATION: Xaa is Asn, Glu, Met, His, Lys, Leu, Ala or Val.
<220> FEATURE:
<221> NAME/KEY: misc_feature
<222> LOCATION: (56)..(56)
<223> OTHER INFORMATION: Xaa is Gly or Ala.

<400> SEQUENCE: 44

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Xaa Xaa Xaa Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Gly Tyr Gly Ser Ser Tyr Arg Trp Phe Asp Tyr Trp Gly
            100                 105                 110

Gln Gly Thr Leu Val Thr Val Ser Ser
        115                 120
```

<210> SEQ ID NO 45
<211> LENGTH: 121
<212> TYPE: PRT
<213> ORGANISM: Artificial sequence
<220> FEATURE:
<223> OTHER INFORMATION: h1701-007/h1701-008 heavy chain variable region CDR2 mutant

```
<220> FEATURE:
<221> NAME/KEY: misc_feature
<222> LOCATION: (54)..(54)
<223> OTHER INFORMATION: Xaa is Asn, Leu, Val, Met or Glu.
<220> FEATURE:
<221> NAME/KEY: misc_feature
<222> LOCATION: (55)..(55)
<223> OTHER INFORMATION: Xaa is Asn, Glu, Met, His, Lys, Leu, Ala or
      Val.
<220> FEATURE:
<221> NAME/KEY: misc_feature
<222> LOCATION: (56)..(56)
<223> OTHER INFORMATION: Xaa is Gly or Ala.

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Ile Pro Xaa Xaa Xaa Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 46
<211> LENGTH: 121
<212> TYPE: PRT
<213> ORGANISM: Artificial sequence
<220> FEATURE:
<223> OTHER INFORMATION: h1701-009/h1701-010 heavy chain variable region
      CDR2 mutant
<220> FEATURE:
<221> NAME/KEY: misc_feature
<222> LOCATION: (54)..(54)
<223> OTHER INFORMATION: Xaa is Asn, Leu, Val, Met or Glu.
<220> FEATURE:
<221> NAME/KEY: misc_feature
<222> LOCATION: (55)..(55)
<223> OTHER INFORMATION: Xaa is Asn, Glu, Met, His, Lys, Leu, Ala or
      Val.
<220> FEATURE:
<221> NAME/KEY: misc_feature
<222> LOCATION: (56)..(56)
<223> OTHER INFORMATION: Xaa is Gly or Ala.

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Xaa Xaa Xaa Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 47
<211> LENGTH: 121
<212> TYPE: PRT
<213> ORGANISM: Artificial sequence
<220> FEATURE:
<223> OTHER INFORMATION: h1701-011/h1701-012 heavy chain variable region
      CDR2 mutant
<220> FEATURE:
<221> NAME/KEY: misc_feature
<222> LOCATION: (54)..(54)
<223> OTHER INFORMATION: Xaa is Asn, Leu, Val, Met or Glu.
<220> FEATURE:
<221> NAME/KEY: misc_feature
<222> LOCATION: (55)..(55)
<223> OTHER INFORMATION: Xaa is Asn, Glu, Met, His, Lys, Leu, Ala or
      Val.
<220> FEATURE:
<221> NAME/KEY: misc_feature
<222> LOCATION: (56)..(56)
<223> OTHER INFORMATION: Xaa is Gly or Ala.

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Ile Pro Xaa Xaa Xaa Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 48
<211> LENGTH: 121
<212> TYPE: PRT
<213> ORGANISM: Artificial sequence
<220> FEATURE:
<223> OTHER INFORMATION: h1701-013/h1701-014 heavy chain variable region
      CDR2 mutant
<220> FEATURE:
<221> NAME/KEY: misc_feature
<222> LOCATION: (54)..(54)
<223> OTHER INFORMATION: Xaa is Asn, Leu, Val, Met or Glu.
<220> FEATURE:
<221> NAME/KEY: misc_feature
<222> LOCATION: (55)..(55)
<223> OTHER INFORMATION: Xaa is Asn, Glu, Met, His, Lys, Leu, Ala or
      Val.
<220> FEATURE:
<221> NAME/KEY: misc_feature
<222> LOCATION: (56)..(56)
<223> OTHER INFORMATION: Xaa is Gly or Ala.
```

<400> SEQUENCE: 48

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Lys Gln Ala Pro Gly Gln Gly Leu Glu Trp Ile
        35                  40                  45

Gly Asp Ile Ile Pro Xaa Xaa Xaa Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120
```

<210> SEQ ID NO 49
<211> LENGTH: 121
<212> TYPE: PRT
<213> ORGANISM: Artificial sequence
<220> FEATURE:
<223> OTHER INFORMATION: h1701-015/h1701-016 heavy chain variable region CDR2 mutant
<220> FEATURE:
<221> NAME/KEY: misc_feature
<222> LOCATION: (54)..(54)
<223> OTHER INFORMATION: Xaa is Asn, Leu, Val, Met or Glu.
<220> FEATURE:
<221> NAME/KEY: misc_feature
<222> LOCATION: (55)..(55)
<223> OTHER INFORMATION: Xaa is Asn, Glu, Met, His, Lys, Leu, Ala or Val.
<220> FEATURE:
<221> NAME/KEY: misc_feature
<222> LOCATION: (56)..(56)
<223> OTHER INFORMATION: Xaa is Gly or Ala.

<400> SEQUENCE: 49

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Ala Asp Ile Ile Pro Xaa Xaa Xaa Gly Ser Lys Tyr Asn Gln Lys Phe
    50                  55                  60

Lys Asp Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120
```

<210> SEQ ID NO 50
<211> LENGTH: 121
<212> TYPE: PRT
<213> ORGANISM: Artificial sequence

```
<220> FEATURE:
<223> OTHER INFORMATION: h1701-017/h1701-018 heavy chain variable region
      CDR2 mutant
<220> FEATURE:
<221> NAME/KEY: misc_feature
<222> LOCATION: (54)..(54)
<223> OTHER INFORMATION: Xaa is Asn, Leu, Val, Met or Glu
<220> FEATURE:
<221> NAME/KEY: misc_feature
<222> LOCATION: (55)..(55)
<223> OTHER INFORMATION: Xaa is Asn, Glu, Met, His, Lys, Leu, Ala or Val
<220> FEATURE:
<221> NAME/KEY: misc_feature
<222> LOCATION: (56)..(56)
<223> OTHER INFORMATION: Xaa is Gly or Ala

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Lys Gln Ala Pro Gly Gln Gly Leu Glu Trp Ile
        35                  40                  45

Ala Asp Ile Ile Pro Xaa Xaa Xaa Gly Ser Lys Tyr Asn Gln Lys Phe
    50                  55                  60

Lys Asp Arg Ala Thr Leu Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 51
<211> LENGTH: 121
<212> TYPE: PRT
<213> ORGANISM: Artificial sequence
<220> FEATURE:
<223> OTHER INFORMATION: h1701-009 NLG heavy chain variable region

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn Leu Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 52
<211> LENGTH: 121
```

```
<212> TYPE: PRT
<213> ORGANISM: Artificial sequence
<220> FEATURE:
<223> OTHER INFORMATION: h1701-009 NVG heavy chain variable region

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn Val Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 53
<211> LENGTH: 121
<212> TYPE: PRT
<213> ORGANISM: Artificial sequence
<220> FEATURE:
<223> OTHER INFORMATION: h1701-009 NNA heavy chain variable region

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn Asn Ala Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 54
<211> LENGTH: 121
<212> TYPE: PRT
<213> ORGANISM: Artificial sequence
<220> FEATURE:
<223> OTHER INFORMATION: h1701-009NMA heavy chain variable region

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
```

```
            20                  25                  30

Tyr Met Asn Trp Val Arg Gln Ala Pro Gly Gln Gly Leu Glu Trp Met
        35                  40                  45

Gly Asp Ile Ile Pro Asn Met Ala Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 55
<211> LENGTH: 121
<212> TYPE: PRT
<213> ORGANISM: Artificial sequence
<220> FEATURE:
<223> OTHER INFORMATION: h1701-009 NEA heavy chain variable region

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn Glu Ala Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 56
<211> LENGTH: 121
<212> TYPE: PRT
<213> ORGANISM: Artificial sequence
<220> FEATURE:
<223> OTHER INFORMATION: h1701-009 NHA heavy chain variable region

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn His Ala Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 57
<211> LENGTH: 121
<212> TYPE: PRT
<213> ORGANISM: Artificial sequence
<220> FEATURE:
<223> OTHER INFORMATION: h1701-009 NMG heavy chain variable region

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn Met Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 58
<211> LENGTH: 121
<212> TYPE: PRT
<213> ORGANISM: Artificial sequence
<220> FEATURE:
<223> OTHER INFORMATION: h1701-009 NEG heavy chain variable region

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn Glu Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 59
```

```
<211> LENGTH: 121
<212> TYPE: PRT
<213> ORGANISM: Artificial sequence
<220> FEATURE:
<223> OTHER INFORMATION: h1701-009 NKG heavy chain variable region

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn Lys Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 60
<211> LENGTH: 121
<212> TYPE: PRT
<213> ORGANISM: Artificial sequence
<220> FEATURE:
<223> OTHER INFORMATION: h1701-009 NAG heavy chain variable region

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn Ala Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 61
<211> LENGTH: 121
<212> TYPE: PRT
<213> ORGANISM: Artificial sequence
<220> FEATURE:
<223> OTHER INFORMATION: h1701-009 NHG heavy chain variable region

<400> SEQUENCE: 61

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Ile Ile Pro Asn His Gly Gly Ser Lys Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Trp Gly Tyr Gly Ser Ser Tyr Arg Trp Phe Asp Tyr Trp Gly
            100                 105                 110

Gln Gly Thr Leu Val Thr Val Ser Ser
        115                 120


<210> SEQ ID NO 62
<211> LENGTH: 17
<212> TYPE: PRT
<213> ORGANISM: Artificial sequence
<220> FEATURE:
<223> OTHER INFORMATION: h1701-009 NLG HCDR2

<400> SEQUENCE: 62

Asp Ile Ile Pro Asn Leu Gly Gly Ser Lys Tyr Asn Gln Lys Phe Lys
1               5                   10                  15

Asp


<210> SEQ ID NO 63
<211> LENGTH: 17
<212> TYPE: PRT
<213> ORGANISM: Artificial sequence
<220> FEATURE:
<223> OTHER INFORMATION: h1701-009 NVG HCDR2

<400> SEQUENCE: 63

Asp Ile Ile Pro Asn Val Gly Gly Ser Lys Tyr Asn Gln Lys Phe Lys
1               5                   10                  15

Asp


<210> SEQ ID NO 64
<211> LENGTH: 17
<212> TYPE: PRT
<213> ORGANISM: Artificial sequence
<220> FEATURE:
<223> OTHER INFORMATION: h1701-009 NNA HCDR2

<400> SEQUENCE: 64

Asp Ile Ile Pro Asn Asn Ala Gly Ser Lys Tyr Asn Gln Lys Phe Lys
1               5                   10                  15

Asp


<210> SEQ ID NO 65
<211> LENGTH: 17
<212> TYPE: PRT
<213> ORGANISM: Artificial sequence
<220> FEATURE:
<223> OTHER INFORMATION: h1701-009NMA  HCDR2

<400> SEQUENCE: 65

Asp Ile Ile Pro Asn Met Ala Gly Ser Lys Tyr Asn Gln Lys Phe Lys
1               5                   10                  15
```

Asp

<210> SEQ ID NO 66
<211> LENGTH: 17
<212> TYPE: PRT
<213> ORGANISM: Artificial sequence
<220> FEATURE:
<223> OTHER INFORMATION: h1701-009 NEA HCDR2

<400> SEQUENCE: 66

Asp Ile Ile Pro Asn Glu Ala Gly Ser Lys Tyr Asn Gln Lys Phe Lys
1 5 10 15

Asp

<210> SEQ ID NO 67
<211> LENGTH: 17
<212> TYPE: PRT
<213> ORGANISM: Artificial sequence
<220> FEATURE:
<223> OTHER INFORMATION: h1701-009NHA HCDR2

<400> SEQUENCE: 67

Asp Ile Ile Pro Asn His Ala Gly Ser Lys Tyr Asn Gln Lys Phe Lys
1 5 10 15

Asp

<210> SEQ ID NO 68
<211> LENGTH: 17
<212> TYPE: PRT
<213> ORGANISM: Artificial sequence
<220> FEATURE:
<223> OTHER INFORMATION: h1701-009NMG HCDR2

<400> SEQUENCE: 68

Asp Ile Ile Pro Asn Met Gly Gly Ser Lys Tyr Asn Gln Lys Phe Lys
1 5 10 15

Asp

<210> SEQ ID NO 69
<211> LENGTH: 17
<212> TYPE: PRT
<213> ORGANISM: Artificial sequence
<220> FEATURE:
<223> OTHER INFORMATION: h1701-009NEG HCDR2

<400> SEQUENCE: 69

Asp Ile Ile Pro Asn Glu Gly Gly Ser Lys Tyr Asn Gln Lys Phe Lys
1 5 10 15

Asp

<210> SEQ ID NO 70
<211> LENGTH: 17
<212> TYPE: PRT
<213> ORGANISM: Artificial sequence
<220> FEATURE:
<223> OTHER INFORMATION: h1701-009NKG HCDR2

<400> SEQUENCE: 70

Asp Ile Ile Pro Asn Lys Gly Gly Ser Lys Tyr Asn Gln Lys Phe Lys
1 5 10 15

Asp

<210> SEQ ID NO 71

-continued

```
<211> LENGTH: 17
<212> TYPE: PRT
<213> ORGANISM: Artificial sequence
<220> FEATURE:
<223> OTHER INFORMATION: h1701-009NAG HCDR2

<400> SEQUENCE: 71

Asp Ile Ile Pro Asn Ala Gly Gly Ser Lys Tyr Asn Gln Lys Phe Lys
1               5                   10                  15

Asp


<210> SEQ ID NO 72
<211> LENGTH: 17
<212> TYPE: PRT
<213> ORGANISM: Artificial sequence
<220> FEATURE:
<223> OTHER INFORMATION: h1701-009NHG HCDR2

<400> SEQUENCE: 72

Asp Ile Ile Pro Asn His Gly Gly Ser Lys Tyr Asn Gln Lys Phe Lys
1               5                   10                  15

Asp
```

TIM-3 ANTIBODY, ANTIGEN BINDING FRAGMENT THEREOF, AND MEDICINAL USES THEREOF

CROSS-REFERENCE TO RELATED APPLICATION

This application is a Section 371 of International Application No. PCT/CN2018/077190, filed Feb. 26, 2018, which was published in the Chinese language on Aug. 30, 2018 under International Publication No. WO 2018/153366 A1, which claims priority under 35 U.S.C. § 119(b) to Chinese Application No. 201710108747.2, filed Feb. 27, 2017, and the disclosures of which are incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "688452_119US_Sequence_Listing" and a creation date of Jul. 26, 2019 and having a size of 68.1 kb. The sequence listing submitted via EFS-Web is part of the specification and is herein incorporated by reference in its entirety.

FIELD OF THE INVENTION

The present invention relates to a TIM-3 antibody and antigen-binding fragment thereof. Further, the invention relates to chimeric and humanized antibodies comprising the CDR regions of the TIM-3 antibody, as well as a pharmaceutical composition comprising the TIM-3 antibody and antigen-binding fragment thereof, and their use as diagnostic agents and therapeutic drugs in TIM-3 related diseases.

BACKGROUND OF THE INVENTION

T cell immunoglobulin and mucin domain-containing molecule-3(TIM-3), also known as hepatitis A virus cellular receptor 2 (HAVCR-2), is a type I membrane surface protein molecule, and belongs to a member of TIM family. Human TIM-3 molecule is composed of 301 amino acids, including a signal peptide, an Ig variable region (IgV), a mucin region rich in serine/threonine, a transmembrane domain and a cytoplasmic region, with 63% homology between murine and human.

TIM-3 is selectively expressed on T helper cells (Th1 and Th17) that secrete IFN-γ, T regulatory cells (Treg), dendritic cells (DCs), monocytes, mast cells, NK cells and tumor infiltrating lymphocytes (TILs) (see, e.g., Clayton et al., J. Immunol., 192(2): 782-791 (2014); Jones et al., J. Exp. Med., 205: 2763-2779 (2008)). The currently known TIM-3 receptor comprises phosphatidylserine galactose lectin 9 (Galectin-9, Gal-9), high mobility group protein 1 (HMGB1) and carcinoembryonic antigen cell adhesion molecule 1 (CEACAM1).

TIM-3 can regulate the function of the immune system in many aspects. It can down-regulate the immune response of Th1 cells after binding to the Gal-9 ligand on the surface of Th1 cells, can induce apoptosis of the Th1 cells, and plays an important role in autoimmune diseases (such as systemic lupus erythematosus, asthma) and immune tolerance. TIM-3 expressed by monocyte-macrophages interacts with the phosphatidylserine to promote the cytophagy of apoptotic cells; TIM-3 binds to HMGB1 ligand in tumor infiltrating dendritic cells and inhibits the normal transport of nucleic acids, and thus inhibits nucleic acid immune response and is involved in immune escape. TIM-3 is not only expressed on immune cells, but also expressed on ovarian cancer, meningioma, melanoma and other tumor cells, and directly promotes the growth of tumors. Down-regulation of TIM-3 expression significantly inhibits the invasion and metastasis of Hela cells. Over-expression of TIM-3 was closely correlated with poor prognoses in lung cancer, gastric cancer, prostate cancer and cervical cancer. In hematological malignancies, TIM-3 is over-expressed on leukemia stem cells from patients with acute myeloid leukemia and on hematopoietic stem cells from MDS (myelodysplastic syndrome) patients; and TIM-3$^+$ hematopoietic stem cells have malignant biological characteristics such as low differentiation, low apoptosis and high proliferation. Therefore, inhibiting the activity of TIM-3 (such as TIM-3 antibody) to improve the function of the inherent immune system, is a promising new method for treating tumors (see, e.g., Ngiow et al., Cancer Res., 71(21): 1-5 (2011); Guo et al., Journal of Translational Medicine, 11: 215 (2013); and Ngiow et al., Cancer Res., 71(21): 6567-6571 (2011)).

The stability of antibody-based drugs is one of the key factors affecting the druggability, wherein the nonenzymatic deamidation of asparagine (Asn) and glutamine (Gln) can cause the instability and the heterogeneity of the antibody, and is one of the common chemical degradation pathways of antibody molecules. It was reported that multiple IgG1 subtype antibodies lost their biological activities due to the deamidation and isomerization of amino acids in CDR regions. Huang et al. found that the deamidation of Asn55 located in heavy chain variable region 2 (CDR2) of IgG1 monoclonal antibody significantly decreased the binding activity thereof. Therefore, in the process of developing an antibody, one should avoid the corresponding amino acids, or alter them, to reduce the occurrence of deamidation, and to increase the stability and bioavailability of the antibody.

Although there are several patents in which the TIM-3 antibody has been reported, for example, WO2011159877, WO2013006490, WO2015117002, WO2016144803, WO2016161270, US20150218274, in China and overseas, there are only two TIM-3 antibodies in the clinical research stage, other antibody-based drugs are still in the discovery and research stage and there is no TIM-3 antibody present in clinical application. Therefore, it is necessary to develop further TIM-3 antibodies with higher activity, higher affinity and higher stability for therapy research and application in TIM-3 related diseases.

SUMMARY OF THE INVENTION

The present invention provides a monoclonal antibody or antigen-binding fragment thereof which binds to the amino acid residues or the three-dimensional structure of the extracellular region of TIM-3. In addition, the present invention provides an anti-human TIM-3 antibody having high activity and high stability by screening for anti-human TIM-3 antibody that competes with the present monoclonal antibody or the antibody fragments thereof.

In addition, the present invention provides a hybridoma producing an antibody of the present invention, a DNA encoding an antibody of the present invention, a vector comprising the DNA, a transformant obtained by transforming the vector, a method for producing an antibody or antibody fragments thereof by using the hybridoma or the transformant, and a diagnostic agent or a therapeutic agent by using the antibody or antibody fragments thereof.

In one aspect, the present invention provides a TIM-3 antibody or antigen-binding fragment that binds to the extracellular region of human TIM-3 and competes with a monoclonal antibody or antigen-binding fragment thereof selected from the following (i) to (iv); or is a monoclonal antibody or antigen-binding fragment thereof selected from the following (i) to (iv):

(i) a monoclonal antibody or antigen-binding fragment thereof, comprising one or more CDR region sequences selected from the following sequences or selected from the amino acid sequences with at least 95% identity to the following:

heavy chain variable region HCDR sequences as shown in SEQ ID NOs: 8, 43 and 10; and light chain variable region LCDR sequences as shown in SEQ ID NOs: 11, 12 and 13;

(ii) a monoclonal antibody or antigen-binding fragment thereof, comprising one or more CDR region sequences selected from the following sequences or selected from the sequences with at least 95% identity to the following:

heavy chain variable region HCDR sequences as shown in SEQ ID NOs: 14, 15 and 16; and light chain variable region LCDR sequences as shown in SEQ ID NOs: 17, 18 and 19;

(iii) a monoclonal antibody or antigen-binding fragment thereof, comprising heavy chain variable region HCDR1-3 sequences as shown in SEQ ID NOs: 8, 43 and 10, respectively; and light chain variable region LCDR1-3 sequences as shown in SEQ ID NOs: 11, 12 and 13, respectively;

(iv) a monoclonal antibody or antigen-binding fragment thereof, comprising heavy chain variable region HCDR1-3 sequences as shown in SEQ ID NOs: 14, 15 and 16, respectively; and light chain variable region LCDR1-3 sequences as shown in SEQ ID NOs: 17, 18 and 19, respectively.

In one aspect, the invention provides a TIM-3 antibody or antigen-binding fragment thereof that binds to the extracellular domain of human TIM-3 and competes with a monoclonal antibody or antigen binding fragment thereof selected from the group consisting of the following (a) to (m), or is a monoclonal antibody or antigen-binding fragment thereof selected from the following (a) to (m):

(a) a monoclonal antibody or antigen-binding fragment thereof comprising the antibody heavy chain variable region HCDR1-3 sequences as shown in SEQ ID NOs: 8, 9 and 10, respectively, and the antibody light chain variable region LCDR1-3 sequences as shown in SEQ ID NOs: 11, 12 and 13, respectively;

(b) a monoclonal antibody or antigen-binding fragment thereof comprising the antibody heavy chain variable region HCDR1-3 sequences as shown in SEQ ID NOs: 8, 62 and 10, respectively, and the antibody light chain variable region LCDR1-3 sequences as shown in SEQ ID NOs: 11, 12 and 13, respectively;

(c) a monoclonal antibody or antigen-binding fragment thereof comprising the antibody heavy chain variable region HCDR1-3 sequences as shown in SEQ ID NOs: 8, 63 and 10, respectively, and the antibody light chain variable region LCDR1-3 sequences as shown in SEQ ID NOs: 11, 12 and 13, respectively;

(d) a monoclonal antibody or antigen-binding fragment thereof comprising the antibody heavy chain variable region HCDR1-3 sequences as shown in SEQ ID NOs: 8, 64 and 10, respectively, and the antibody light chain variable region LCDR1-3 sequences as shown in SEQ ID NOs: 11, 12 and 13, respectively;

(e) a monoclonal antibody or antigen-binding fragment thereof comprising the antibody heavy chain variable region HCDR1-3 sequences as shown in SEQ ID NOs: 8, 65 and 10, respectively, and the antibody light chain variable region LCDR1-3 sequences as shown in SEQ ID NOs: 11, 12 and 13, respectively;

(f) a monoclonal antibody or antigen-binding fragment thereof comprising the antibody heavy chain variable region HCDR1-3 sequences as shown in SEQ ID NOs: 8, 66 and 10, respectively, and the antibody light chain variable region LCDR1-3 sequences as shown in SEQ ID NOs: 11, 12 and 13, respectively;

(g) a monoclonal antibody or antigen-binding fragment thereof comprising the antibody heavy chain variable region HCDR1-3 sequences as shown in SEQ ID NOs: 8, 67 and 10, respectively, and the antibody light chain variable region LCDR1-3 sequences as shown in SEQ ID NOs: 11, 12 and 13, respectively;

(h) a monoclonal antibody or antigen-binding fragment thereof comprising the antibody heavy chain variable region HCDR1-3 sequences as shown in SEQ ID NOs: 8, 68 and 10, respectively, and the antibody light chain variable region LCDR1-3 sequences as shown in SEQ ID NOs: 11, 12 and 13, respectively;

(i) a monoclonal antibody or antigen-binding fragment thereof comprising the antibody heavy chain variable region HCDR1-3 sequences as shown in SEQ ID NOs: 8, 69 and 10, respectively, and the antibody light chain variable region LCDR1-3 sequences as shown in SEQ ID NOs: 11, 12 and 13, respectively;

(g) a monoclonal antibody or antigen-binding fragment thereof comprising the antibody heavy chain variable region HCDR1-3 sequences as shown in SEQ ID NOs: 8, 70 and 10, respectively, and the antibody light chain variable region LCDR1-3 sequences as shown in SEQ ID NOs: 11, 12 and 13, respectively;

(k) a monoclonal antibody or antigen-binding fragment thereof comprising the antibody heavy chain variable region HCDR1-3 sequences as shown in SEQ ID NOs: 8, 71 and 10, respectively, and the antibody light chain variable region LCDR1-3 sequences as shown in SEQ ID NOs: 11, 12 and 13, respectively;

(l) a monoclonal antibody or antigen-binding fragment thereof comprising the antibody heavy chain variable region HCDR1-3 sequences as shown in SEQ ID NOs: 8, 72 and 10, respectively, and the antibody light chain variable region LCDR1-3 sequences as shown in SEQ ID NOs: 11, 12 and 13, respectively; and (m) a monoclonal antibody or antigen-binding fragment thereof comprising the antibody heavy chain variable region HCDR1-3 sequences as shown in SEQ ID NOs: 14, 15 and 16, respectively, and the antibody light chain variable region LCDR1-3 sequences as shown in SEQ ID NOs: 17, 18 and 19, respectively.

In a preferred embodiment of the present invention, provided is a TIM-3 antibody or antigen binding fragments thereof described herein, wherein the TIM-3 antibody or antigen binding fragment thereof binds to the same epitope to which a monoclonal antibody selected from the above (i) to (iv) binds.

In a preferred embodiment of the present invention, provided is a TIM-3 antibody or antigen binding fragment thereof described herein, wherein the monoclonal antibody is a recombinant antibody.

In a preferred embodiment of the present invention, provided is a TIM-3 antibody or antigen binding fragment thereof described herein, wherein the monoclonal antibody is selected from the group consisting of a murine antibody, a chimeric antibody, and a recombinant antibody of a humanized antibody, or an antigen-binding fragment thereof.

In a preferred embodiment of the present invention, provided is a humanized TIM-3 antibody or antigen binding fragment thereof described herein, wherein the framework (FR) sequences of the light chain and the heavy chain variable region of the humanized antibody are derived from a human germline light chain and heavy chain, respectively, or a mutant sequence thereof.

In a preferred embodiment of the present invention, provided is a humanized TIM-3 antibody or antigen binding fragment thereof described herein, wherein the humanized antibody comprises a heavy chain variable region as shown in SEQ ID NO: 44 or 31 or a variant thereof, wherein the variant has 1-10 amino acid mutations on the heavy chain variable region sequence of SEQ ID NO: 44 or 31.

In a preferred embodiment of the present invention, provided is a variant of a TIM-3 antibody or antigen binding fragment thereof described herein, wherein the variant has 1-10 amino acid back-mutations in the FR region of the heavy chain variable region sequence of SEQ ID NO: 44 or 31; preferably, the back-mutation is selected from the group consisting of D89E, R98T, G49A, M48I, M70L, R38K and V68A back-mutations on the heavy chain variable region sequence of SEQ ID NO: 44, or selected from Q3K or R87K back-mutation in the heavy chain variable region sequence of SEQ ID NO: 31.

In a preferred embodiment of the present invention, in order to eliminate chemical modifications, such as acetylation and deamidation, in the CDR regions of a TIM-3 antibody or antigen binding fragment thereof provided herein, the amino acid sites on the CDR regions prone to chemical modifications can be replaced. Preferably, the amino acids NNG in the CDR2 region are replaced. Preferably, provided is a humanized TIM-3 antibody or antigen binding fragment thereof described herein, wherein the humanized antibody comprises a heavy chain variable region sequence selected from any one of SEQ ID NOs: 45-50 or comprises a heavy chain variable region sequence selected from any one of SEQ ID NOs: 34-35.

In a preferred embodiment of the present invention, provided is a humanized TIM-3 antibody or antigen binding fragment thereof described herein, wherein the humanized antibody comprises a light chain variable region as shown in SEQ ID NO: 21 or 32 or a variant thereof, wherein the variant has 1-10 amino acid mutations on the light chain variable region as shown in SEQ ID NO: 21 or 32.

In a preferred embodiment of the present invention, provided is a variant of a TIM-3 antibody or antigen binding fragment thereof described herein, wherein the variant has 1-10 amino acid back-mutations in the FR region of the light chain variable region sequence of SEQ ID NO: 21 or 32; preferably, the back-mutation is selected from A43S back-mutation in the light chain variable region sequence of SEQ ID NO: 21 or selected from the Q3K, I48V, K45Q, A43S and T85S back-mutations in the light chain variable region sequence of SEQ ID NO: 32.

In a preferred embodiment of the present invention, provided is a humanized TIM-3 antibody or antigen binding fragment thereof described herein, wherein the humanized antibody comprises a light chain variable region sequence of SEQ ID NO: 30 or comprises a light chain variable region selected from any one of SEQ ID NOs: 37-40.

In a preferred embodiment of the present invention, in order to eliminate chemical modifications, such as acetylation and deamidation, in the CDR regions of a TIM-3 antibody or antigen binding fragment thereof provided herein, the amino acid sites of the CDR regions prone to chemical modification can be replaced. Preferably, the amino acids NNG in the CDR2 region are replaced and a CDR2 sequence as shown in SEQ ID NO:43 is obtained. Preferably, provided is a humanized antibody of the TIM-3 antibody or antigen binding fragment thereof described herein, wherein the humanized antibody comprises a heavy chain variable region sequence selected from any one of the SEQ ID NOs: 44-50 and a light chain variable region sequence selected from any one of the SEQ ID NOs: 29-30; or comprises a heavy chain variable region sequence selected from any one of SEQ ID NOs: 22-28 and a light chain variable region sequence selected from any one of SEQ ID NOs: 29-30; or comprises a heavy chain variable region sequence selected from any one of the SEQ ID NOs: 33-35 and a light chain variable region sequence selected from any one of the SEQ ID NOs: 36-40; preferably comprises a heavy chain variable region sequence of SEQ ID NO: 24 and a light chain variable region sequence of SEQ ID NO: 29; or comprises a heavy chain variable region sequence of SEQ ID NO: 33 and a light chain variable region sequence of SEQ ID NO: 36.

In a preferred embodiment of the present invention, in order to eliminate deamidation in amino acid sites in the CDR regions of a TIM-3 antibody or antigen binding fragment thereof provided herein, the amino acid sites of the CDR regions prone to deamidation can be replaced. Preferably, the amino acids NNG in the CDR2 is replaced. In a preferred embodiment, provided is a humanized antibody of a TIM-3 antibody or antigen binding fragment thereof described herein, wherein the humanized antibody comprises a heavy chain variable region selected from any one of SEQ ID NOs: 51-61 and a light chain variable region selected from any one of SEQ ID NOs: 29-30; preferably comprises a heavy chain variable region sequence of SEQ ID NO: 51 and a light chain variable region sequence of SEQ ID NO: 29; or comprises a heavy chain variable region sequence of SEQ ID NO: 52 and a light chain variable region sequence of SEQ ID NO: 29.

In a preferred embodiment of the present invention, the TIM-3 antibody or antigen binding fragment thereof provided herein is a full-length antibody, which comprises a constant region of the human antibody. Preferably, the antibody comprises a human heavy chain constant region sequence as shown in SEQ ID NO:41. Preferably, the antibody comprises a human light chain constant region sequence as shown in SEQ ID NO:42.

In a preferred embodiment of the present invention, provided is a TIM-3 antibody or antigen binding fragments thereof described herein, wherein the antigen-binding fragment is selected from the group consisting of Fab, Fab', $F(ab')_2$, single-chain antibody (scFv), dimerized V region (diabody), disulfide-stabilized V region (dsFv) and a CDR-containing peptide.

The present invention further provides a pharmaceutical composition which comprises a therapeutically effective amount of the TIM-3 antibody or antigen binding fragment thereof as described herein and one or more pharmaceutically acceptable excipients, diluents or carriers.

The present invention further provides a nucleic acid molecule which encodes a TIM-3 antibody or antigen binding fragment thereof described above.

The present invention further provides a recombinant vector which comprises a nucleic acid molecule as described above.

The present invention further provides a host cell transformed with a recombinant vector as described above, wherein the host cell is selected from the group consisting of prokaryotic cells and eukaryotic cells, preferably eukaryotic cells, more preferably mammalian cells.

The present invention further provides a method for producing an antibody or an antigen-binding fragment thereof as described above, which comprises culturing a host cell as described above in a culture to form and accumulate the antibody or the antigen-binding fragment thereof as described above and recovering the antibody or the antigen-binding fragment thereof from the culture.

The present invention further provides a method for immune assay or measurement of human TIM-3, the method comprises using an antibody or antigen-binding fragment thereof as described above.

The present invention further provides a reagent for detecting or measuring human TIM-3, the reagent comprises the antibody or antigen-binding fragment thereof as described above.

The present invention further provides a diagnostic agent for use in the detection of a disease related to human TIM-3 positive cells, wherein the diagnostic agent comprises the antibody or antigen-binding fragment thereof as described above.

The present invention further provides a method for diagnosing a disease related to human TIM-3 positive cells, wherein the method comprises detecting or measuring human TIM-3 positive cells by using the antibody or the antibody fragment thereof as described in any one of the above.

The present invention further provides use of the antibody or antigen-binding fragment thereof described above for the manufacture of a diagnostic agent for a disease related to human TIM-3 positive cells.

The present invention further provides a therapeutic agent for use in a disease related to human TIM-3 positive cells, wherein the therapeutic agent comprises the antibody or antigen-binding fragment thereof, the composition, or the nucleic acid molecule as described above.

The present invention further provides a method for treating diseases related to human TIM-3 positive cells, wherein the method includes inducing human TIM-3 positive cell death with the antibody or antigen-binding fragment thereof or the composition or the nucleic acid molecule as described above.

The present invention further provides use of the antibody or antigen-binding fragment thereof or the composition or the nucleic acid molecule as described above for the manufacture of a therapeutic agent for the treatment of a disease related to human TIM-3 positive cells.

DRAWING DESCRIPTION

FIG. 1: Experimental curve of the binding of candidate TIM-3 antibodies to cells; the data shows that both the candidate antibody mAb-1701 and mAb-1799 had strong binding activities to the antigen-expressing cells.

Figure 2A:
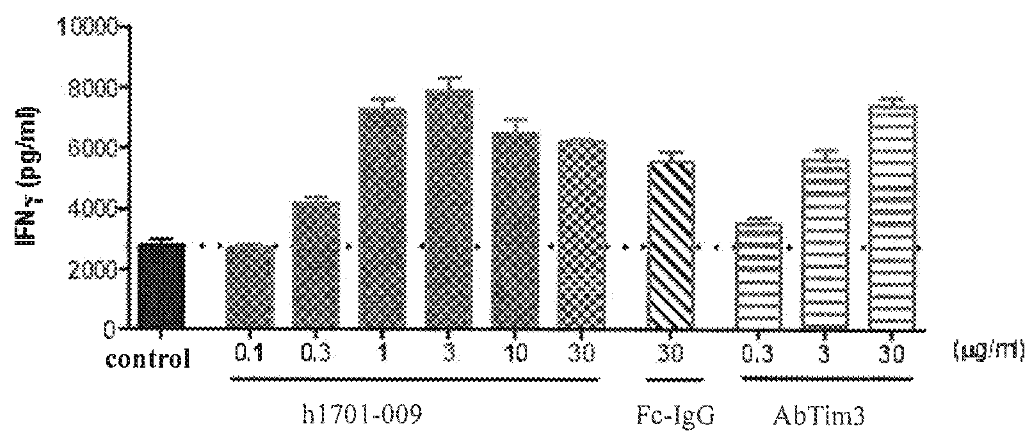
Figure 2B:
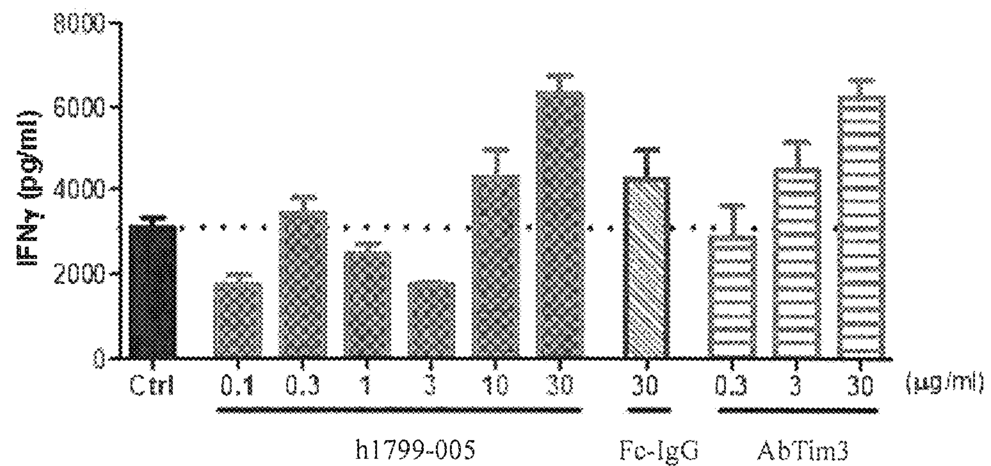
Figure 2C:
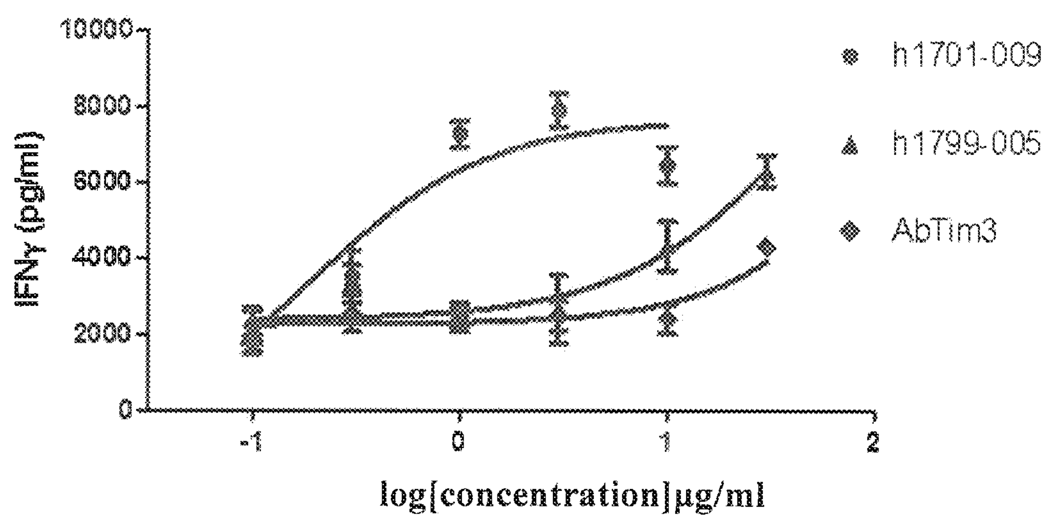
Figure 3A:
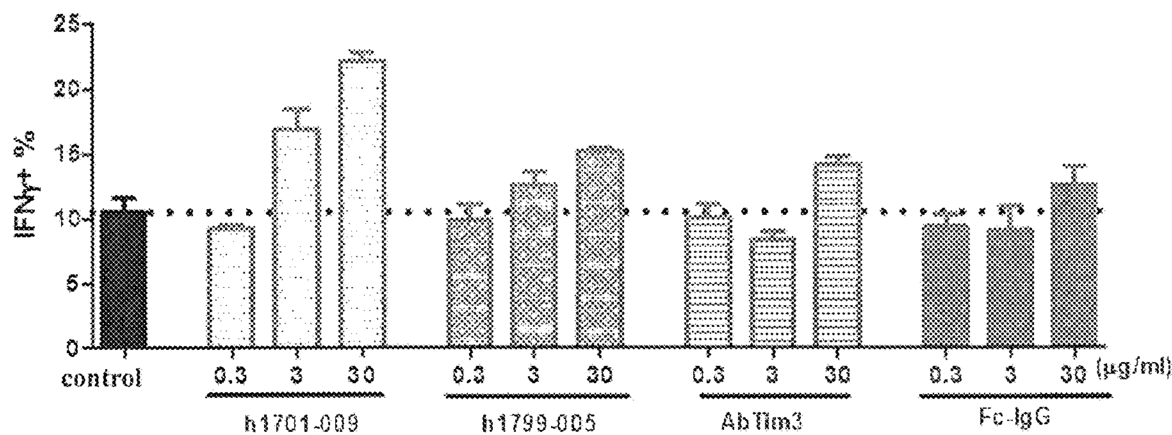
Figure 3B:
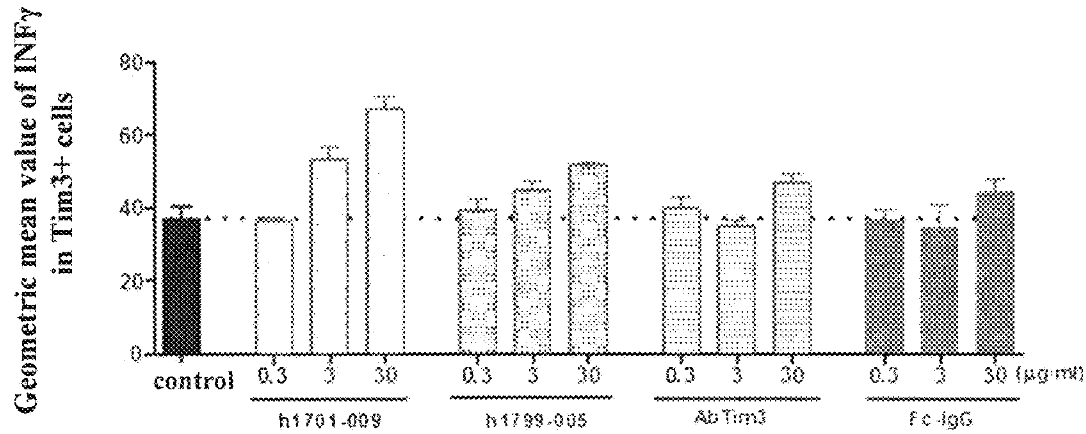
Figure 3C:
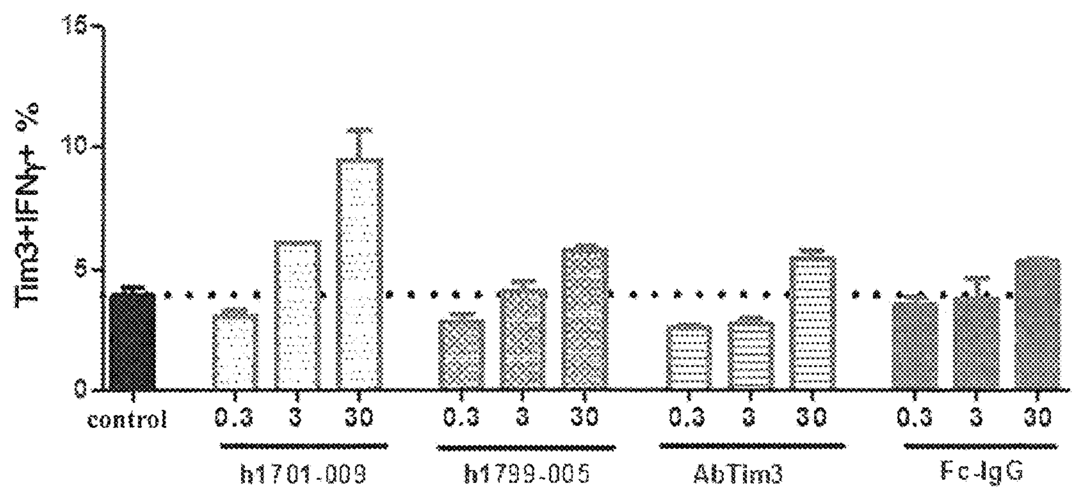
Figure 3D:
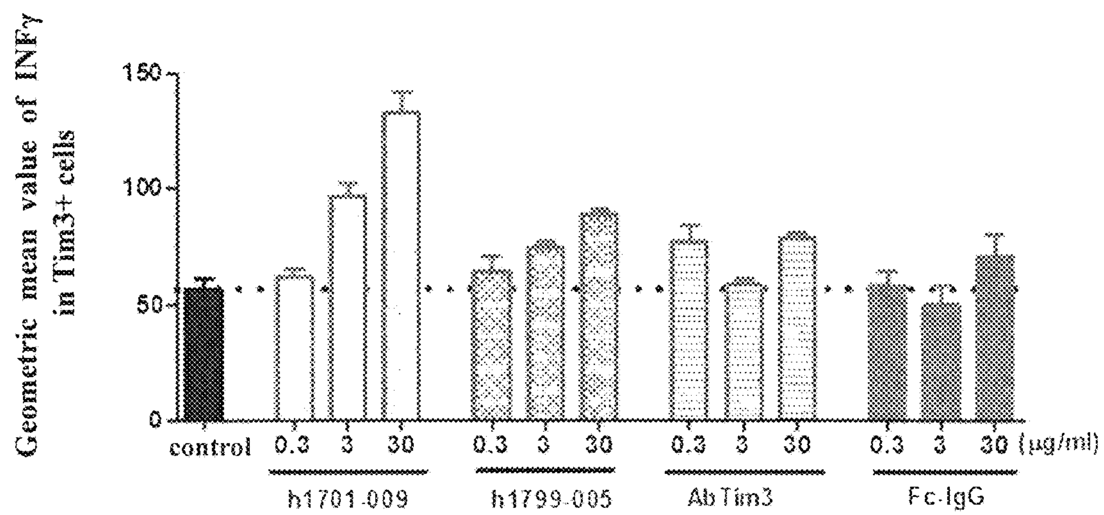

FIGS. 2A-2C: Effect of candidate antibodies and antigen-binding fragments thereof of the present invention on the secretion of IFNγ in the mixed lymphocyte reaction experiments. FIG. 2A: Effect of h1701-009 and antigen-binding fragment thereof on the secretion of IFNγ; FIG. 2B: Effect of h1701-005 and antigen-binding fragment thereof on the secretion of IFNγ; FIG. 2C: Effect of h1701-009 and h1799-005 on the secretion of IFNγ. The results show that both h1701-009 and h1799-005 can effectively stimulate the secretion of IFNγ.

FIGS. 3A-3D: PBMCs were activated by CD3/CD28 antibody. The effect of h1701-009, h1799-005 and AbTIM-3 on the expression of IFNγ in the activated PBMCs. In all of them, the percentage of the IFNγ positive cells as well as the expression of IFNγ increased to different degrees.

Figure 4A:
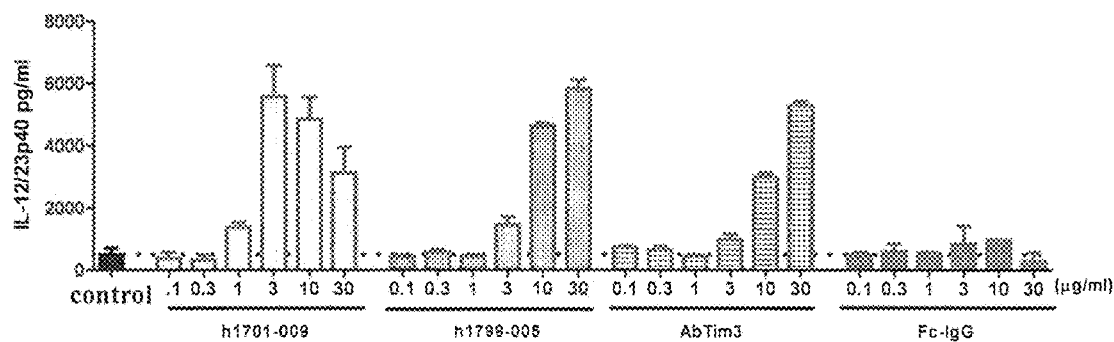
Figure 4B:
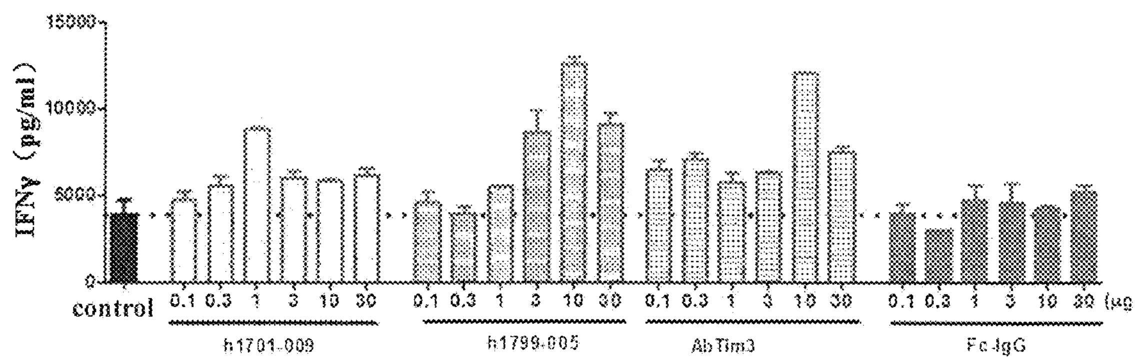

FIGS. 4A-4B: Five days after stimulating PBMCs with SEB, h1701-009, h1799-005 and AbTIM-3 all increased the secretion of SEB-induced IL12 and IFNγ.

DETAILED DESCRIPTION OF THE INVENTION

Terms

For the invention to be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, the single-letter code and the three-letter code for amino acids are as described in J. Biol. Chem, 243, (1968) p3558.

As used herein, "antibody" refers to immunoglobulin, a four-peptide chain structure connected together by disulfide bonds between two identical heavy chains and two identical light chains. Different immunoglobulin heavy chain constant regions exhibit different amino acid compositions and rank orders, hence present different kinds of antigenicity. Accordingly, immunoglobulins can be divided into five types, also called immunoglobulin isotypes, namely IgM, IgD, IgG, IgA and IgE, with the corresponding heavy chain μ, δ, γ, α and ε, respectively. According to its amino acid composition of the hinge region and the number and location of heavy chain disulfide bonds, the same type of Ig can further be divided into different sub-types, for example, IgG can be divided into IgG1, IgG2, IgG3 and IgG4. Light chain can be divided into κ or λ chain considering different constant regions. Each of five types of Ig may have κ or λ chain.

In the present invention, the antibody light chain mentioned herein further comprises a light chain constant region, which comprises a human or murine κ, λ chain or a variant thereof.

In the present invention, the antibody heavy chain mentioned herein further comprises a heavy chain constant region, which comprises human or murine IgG1, IgG 2, IgG 3, IgG 4 or a variant thereof.

Near the N-terminus of the antibody heavy and light chain, about 110 of amino acids change largely, and are known as the variable region (Fv region); the rest of the amino acid residues near the C-terminus are relatively stable, and are known as the constant region. Variable region comprises three hypervariable regions (HVR) and four relatively conserved FR regions (FR). Three hypervariable regions, also known as complementarity determining regions (CDRs), determine the specificity of the antibody. Each light chain variable region (LCVR) and each heavy chain variable region (HCVR) is composed of three CDR regions and four FR regions, arranged from the amino terminus to the carboxyl terminus in the order of: FR1, CDR1, FR2, CDR2, FR3, CDR3, and FR4. Three light chain CDR regions are referred to as LCDR1, LCDR2, and LCDR3; three heavy chain CDR regions are referred to as HCDR1, HCDR2 and HCDR3. The number and location of CDR region amino acid residues in LCVR and HCVR regions of the antibody or antigen binding fragment herein comply with the known Kabat numbering criteria (LCDR1-3, HCDE2-3), or comply with Kabat and Chothia numbering criteria (HCDR1).

An antibody of the present invention can be a murine antibody, chimeric antibody and humanized antibody, preferably it is a humanized antibody.

The term "murine antibody" in the present invention refers to anti-human TIM-3 monoclonal antibody prepared according to the knowledge and skills of the field. During the preparation, test subject was injected with TIM-3 antigen, and then a hybridoma expressing the antibody that possesses the desired sequence or functional characteristics was isolated. In a preferred embodiment of the present invention, the murine TIM-3 antibody or antigen binding fragment thereof further comprises light chain constant region of murine x, 2\, chain or a variant thereof, or further comprises heavy chain constant region of murine IgG1, IgG2, IgG3 or IgG4, or a variant thereof.

The term "chimeric antibody", is an antibody formed by fusing the variable region of murine antibody together with constant region of human antibody, and the chimeric antibody can alleviate the murine antibody-induced immune response. To establish chimeric antibody, a hybridoma secreting a specific murine monoclonal antibody is established and a variable region gene is cloned from the murine hybridoma. Then a desired constant region gene of human antibody is cloned, and connected with the variable region gene of a murine antibody to form a chimeric gene which can be subsequently inserted into an expression vector. Finally the chimeric antibody molecule is expressed in the eukaryotic or prokaryotic system. In a preferred embodiment of the present invention, the light chain of the TIM-3 chimeric antibody further comprises the light chain constant regions derived from a human is 2\, chain or a variant thereof. The heavy chain of TIM-3 chimeric antibody further comprises the heavy chain constant regions derived from human IgG1, IgG2, IgG3, IgG4 or a variant thereof, preferably comprises heavy chain constant region derived from human IgG1, IgG2, IgG4 or a variant thereof after amino acid mutation, such as YTE mutation or back-mutation.

The term "humanized antibody", also known as CDR-grafted antibody, refers to an antibody generated by murine CDR sequences grafted into human antibody variable region framework, i.e., an antibody produced in different types of human germline antibody framework sequences. Humanized antibody conquers the disadvantageously strong antibody response induced by chimeric antibody which carries a large number of murine components. Such framework sequences can be obtained from public DNA database covering germline antibody gene sequences or published references. For example, germline DNA sequences of human heavy and light chain variable region genes can be found in "VBase" human germline sequence database (available on web www.mrccpe.com.ac.uk/vbase), as well as found in Kabat, EA, etc. 1991 Sequences of Proteins of Immunological Interest, 5th Ed. To avoid the decreased activity due to the immunogenic declination, human antibody variable region framework is subjected to a minimum back mutation to remain the activity. The humanized antibody of the present invention also comprises a humanized antibody which is further subjected to CDR affinity maturation by phage display.

In a preferred embodiment of the invention, the murine CDR sequences of TIM-3 humanized antibody are selected from the group consisting of SEQ ID NOs: 8-13 and 14-19. Human antibody variable region frameworks were designed and selected, wherein the heavy chain FR region sequence is derived from combination sequence of human germline heavy chain IGHV1-18*01 and hjh4.1 or combination sequence of IGHV3-7*01 and hjh4.1; the light chain FR region sequence is derived from combination sequence of human germline light chain IGKV1-33*01 and hjk4.1 or combination sequence of IGKV1-39*01 and hjk2.1. To avoid the decreased activity due to the immunogenic declination, the human antibody variable region is subjected to a minimum back mutation to maintain the activity.

The graft of CDR can result in the decrease of the affinity of the TIM-3 antibody or antigen binding fragment thereof to the antigen due to the framework residues contacted with the antigen. Such interactions may be the result of highly somatic mutations. Therefore, it may still be necessary to transfer the donor framework amino acids to the humanized antibody framework. The amino acid residues involved in antigen binding from non-human TIM-3 antibody or antigen binding fragment thereof can be identified by checking the sequence and structure of murine monoclonal antibody variable region. The amino acid residues that are different between the donor CDR framework and the germ lines can be considered to be related. If it is not possible to determine the most closely related germ line, the sequence can be compared with the common sequence of the subtype or the sequence of the murine with high similarity percentage. Rare framework residues are thought to be the result of a high mutation rate in somatic cells, which play an important role in binding.

As used herein, "antigen-binding fragment" or "functional fragment" refers to one or more fragments of the antibody retaining the binding ability to the antigen (e.g. TIM-3). It has been shown that fragments of full-length antibody can have the function of specific binding to the specific antigen. The examples for the binding fragment in the term "antigen binding fragment" include (i) Fab fragments, a monovalent fragment composed of VL, VH, CL and CH1 domains; (ii) $F(ab')_2$ fragment, a bivalent fragment comprising two Fab fragments linked by a disulfide bond in the hinge region; (iii) Fd fragment, consisting of VH and CH1 domains; (iv) Fv fragment, consisting of VH and VL domains of one-arm antibody; (v) single domain or dAb fragment (Ward et al. (1989) Nature 341:544-546) composed of VH domain; and (vi) a separate complementarity determining region (CDR) and (vii) a combination of two or more separate CDRs optionally linked by a synthetic linker. In addition, although the VL domain and VH domain of the Fv fragment are encoded by two separate genes, they can be linked by a synthetic linker using recombinant methods, generating a single protein chain of a monovalent molecular by pairing the VL and VH domain (called single chain Fv (scFv); see, e.g., Bird et al. (1988) Science 242: 423-426; and Huston et al. (1988) Proc. Natl. Acad. Sci USA 85:5879-5883). This single chain antibody is also intended to be included in the term "antigen binding fragment" of the antibody. Such antibodies are obtained using conventional techniques known in the field, and functional screening of fragments are used in the same way as for the intact antibody. Antigen binding portions can be produced by recombinant DNA technology or by enzymatic or chemical disruption of intact immunoglobulins. Antibodies can be in the form of different phenotypes, e.g., IgG (e.g., IgG1, IgG2, IgG3 or IgG4 subtype), IgA1, IgA2, IgD, IgE or IgM antibodies.

The antigen-binding fragment in the invention includes Fab, $F(ab')_2$, Fab', a single-chain antibody (scFv), a dimerized V region (diabody), a disulfide stabilized V region (dsFv) and a CDR-containing peptide.

Fab is an antibody fragment obtained by treating an IgG antibody molecule with a papain (cleaved at an amino acid residue at position 224 of the H chain). The Fab fragment has a molecular weight of about 50,000 and has antigen binding activity, and Fab fragment, about a half of the N-terminal side of H chain and the entire L chain are bound together through a disulfide bond.

The Fab of the present invention can be produced by treating the monoclonal antibody of the present invention which specifically recognizes human TIM-3 and binds to the extracellular region or three-dimensional structure thereof with papain. Also, the Fab can be produced by inserting DNA encoding Fab of the antibody into a prokaryotic expression vector or a eukaryotic expression vector and introducing the vector into a prokaryote or eukaryote to express the Fab.

An F(ab')2 is an antibody fragment having a molecular weight of about 100,000 and having antigen binding activity and comprising two Fab regions which are bound in the hinge position, obtained by digesting the lower part of two disulfide bonds in the hinge region of IgG with pepsin.

The F(ab')2 of the present invention can be produced by treating the monoclonal antibody of the present invention which specifically recognizes human TIM-3 and binds to the extracellular region or three-dimensional structure thereof with pepsin. Also, the F(ab')2 can be produced by binding to Fab' described below via a thioether bond or a disulfide bond.

A Fab' is an antibody fragment having a molecular weight of about 50,000 and having antigen binding activity. Fab' is obtained by cleaving a disulfide bond at the hinge region of the above F(ab')2. The Fab' of the present invention can be produced by treating the F(ab')2 of the present invention which specifically recognizes TIM-3 and binds to the extracellular region or three-dimensional structure thereof with a reducing agent, such as dithiothreitol.

Also, the Fab' can be produced by inserting DNA encoding Fab' fragment of the antibody into a prokaryotic expression vector or a eukaryotic expression vector and introducing the vector into a prokaryote or eukaryote to express the Fab'.

The term "single chain antibody", "single chain Fv" or "scFv" refers to a molecule comprising an antibody heavy chain variable domain (or region; VH) and an antibody light chain variable domain (or region; VL) connected by a linker. Such scFv molecules have the general structure of $NH_2$-VL-linker-VH-COOH or $NH_2$-VH-linker-VL-COOH. A suitable linker in the prior art consists of repeated GGGGS amino acid sequence or variants thereof, for example, using a variant with 1-4 repeats (Holliger et al. (1993), Proc. Natl. Acad. Sci. USA 90:6444-6448). Other linkers that can be used for the present invention are described by Alfthan et al. (1995), Protein Eng. 8:725-731; Choi et al. (2001), Eur. J. Immunol. 31:94-106; Hu et al. (1996), Cancer Res. 56:3055-3061; Kipriyanov et al. (1999), J. Mol. Biol. 293:41-56 and Roovers et al. (2001), Cancer Immunol.

The scFv of the present invention can be produced by the following steps: obtaining cDNAs encoding VH and VL of the monoclonal antibody of the present invention which specifically recognizes human TIM-3 and binds to the extracellular region or three-dimensional structure thereof, constructing DNA encoding scFv, inserting the DNA into a prokaryotic expression vector or an eukaryotic expression vector, and then introducing the expression vector into a prokaryote or eukaryote to express the scFv.

A diabody is an antibody fragment wherein the scFv is dimerized, and is an antibody fragment having divalent antigen binding activity. In the divalent antigen binding activity, two antigens may be the same or different.

The diabody of the present invention can be produced by the following steps, obtaining cDNAs encoding VH and VL of the monoclonal antibody of the present invention which specifically recognizes human TIM-3 and binds to the extracellular region or three-dimensional structure thereof, constructing DNA encoding scFv so that the length of the linker peptide is 8 or less amino acid residues, inserting the DNA into a prokaryotic expression vector or an eukaryotic expression vector, and then introducing the expression vector into a prokaryote or eukaryote to express the diabody.

A dsFv is obtained by substituting one amino acid residue in each of VH and VL with a cysteine residue, and then connecting the substituted polypeptides via a disulfide bond between the two cysteine residues. The amino acid residue to be substituted with a cysteine residue can be selected based on three-dimensional structure prediction of the antibody in accordance with known methods (Protein Engineering, 7, 697 (1994)).

The dsFv of the present invention can be produced by the following steps: obtaining cDNAs encoding VH and VL of the monoclonal antibody of the present invention which specifically recognizes human TIM-3 and binds to the extracellular region or three-dimensional structure thereof, constructing DNA encoding dsFv, inserting the DNA into a prokaryotic expression vector or an eukaryotic expression vector, and then introducing the expression vector into a prokaryote or eukaryote to express the dsFv.

A CDR-containing peptide is constituted by including one or more regions of CDRs of VH or VL. Peptide comprising plural CDRs can be linked directly or via an appropriate linker peptide.

The CDR-containing peptide of the present invention can be produced by the following steps: constructing DNA encoding CDRs of VH and VL of the monoclonal antibody of the present invention which specifically recognizes human TIM-3 and binds to the extracellular region or three-dimensional structure thereof, inserting the DNA into a prokaryotic expression vector or an eukaryotic expression vector, and then introducing the expression vector into a prokaryote or eukaryote to express the peptide. The CDR-containing peptide can also be produced by a chemical synthesis method such as Fmoc method or tBoc method.

The term "CDR" refers to one of the six hypervariable regions within the variable domains of an antibody that mainly contribute to antigen binding. One of the most commonly used definitions for the six CDRs was provided by Kabat E. A. et al., (1991) Sequences of proteins of immunological interest. NIH Publication 91-3242). As used herein, Kabat's definition of CDRs only apply for CDR1, CDR2 and CDR3 of the light chain variable domain (CDR LI, CDR L2, CDR L3, or L1, L2, L3), as well as for CDR2 and CDR3 of the heavy chain variable domain (CDR H2, CDR H3, or H2, H3).

The term "antibody framework" as used herein refers to the part of the variable domain, either VL or VH, which serves as a scaffold for the antigen binding loops (CDRs) of this variable domain. In essence it is the variable domain without the CDRs.

The term "epitope" or "antigenic determinant" refers to a site on an antigen to which an immunoglobulin or antibody specifically binds (e.g., a specific site on the TNF molecule). An epitope typically includes at least 3, 4, 5, 6, 7, 8, 9, 10, 11, 12, 13, 14 or 15 consecutive or non-consecutive amino acids in a unique spatial conformation. See, e.g., Epitope Mapping Protocols in Methods in Molecular Biology, Vol. 66, G. E. Morris, Ed. (1996).

The terms "specific binding," "selective binding," "selectively binds," and "specifically binds," refer to the binding of an antibody to an epitope on a predetermined antigen. Typically, the antibody binds with an affinity (KD) of approximately less than $10^{-7}$ M, such as approximately less than $10^{-8}$ M, $10^{-9}$M or $10^{-10}$ M or even lower.

The term "KD" or "Kd" refers to the dissociation equilibrium constant of a particular antibody-antigen interaction. Typically, the antibodies of the invention bind to TIM-3 with a dissociation equilibrium constant (KD) of less than approximately $10^{-7}$ M, such as less than approximately $10^{-8}$ M, $10^{-9}$ M or $10^{-10}$ M or even lower, for example, as determined using surface plasmon resonance (SPR) technology in a BIACORE instrument.

The term "competitive binding" refers to an antibody recognizing the same epitope (also known as antigenic determinant) or part of the same epitope of the extracellular domain of human TIM-3 as the one recognized by monoclonal antibody of the present invention and binding to the antigen. Antibodies that bind to the same epitope to which the monoclonal antibodies of the present invention bind are antibodies that recognize and bind to the amino acid sequence of human TIM-3 identified by the monoclonal antibodies of the present invention.

The term "nucleic acid molecule" as used herein refers to DNA molecules and RNA molecules. A nucleic acid molecule may be single-stranded or double-stranded, but preferably is double-stranded DNA. A nucleic acid is "effectively linked" when it is placed into a functional relationship with another nucleic acid sequence. For instance, a promoter or enhancer is effectively linked to a coding sequence if it affects the transcription of the sequence.

The term "vector" refers to a nucleic acid molecule capable of transporting another nucleic acid to which it has been linked. In one embodiment, the vector is a "plasmid" which refers to a circular double stranded DNA loop into which additional DNA segments may be ligated. In another embodiment, the vector is a viral vector, wherein additional DNA segments may be ligated into the viral genome. The vectors disclosed herein are capable of self-replicating in the host cell into which they are introduced (e.g., bacterial vectors having a bacterial replication origin and episomal mammalian vectors) or may be integrated into the genome of a host cell upon introduction into the host cell, and thereby are replicated along with the host genome (e.g., non-episomal mammalian vectors).

Methods for producing and purifying antibodies and antigen-binding fragments are well known in the art and can be found, for example, in Harlow and Lane (1988) Antibodies, A Laboratory Manual, Cold Spring Harbor Laboratory Press, Cold Spring Harbor, N.Y., chapters 5-8 and 15. For example, mice can be immunized with human TIM-3, or fragments thereof, and the resulting antibodies can then be renatured, purified, and sequenced for amino acid sequences by using conventional methods well known in the art. Antigen-binding fragments can also be prepared by conventional methods. The antibody or antigen binding fragments of the present invention are engineered to contain one or more human framework regions (FRs) on CDRs derived from a non-human antibody. Human framework germline sequences can be obtained by aligning human antibody variable germline gene database and MOE software from ImMunoGeneTics (IMGT) via their website http://imgt.cines.fr, or from The Immunoglobulin Facts Book, 2001, ISBN 012441351.

The term "host cell" refers to a cell into which the expression vector has been introduced. Host cells include bacterial, microbial, plant or animal cells. Bacteria that are susceptible to be transformed include members of enterobacteriaceae, such as *Escherichia coli* or *Salmonella* strains; Bacillaceae such as *Bacillus subtilis; Pneumococcus; Streptococcus* and *Haemophilus influenzae*. Suitable microorganisms include *Saccharomyces cerevisiae* and *Pichia pastoris*. Suitable animal host cell lines include CHO (Chinese hamster ovary cell line) and NS0 cells.

The engineered antibodies or antigen binding fragments of the present invention may be prepared and purified using known methods. For example, cDNA sequences encoding a heavy chain and a light chain may be cloned and engineered into a GS expression vector. The engineered immunoglobulin expression vector may then be stably transfected in CHO cells. As a more recommended method well known in the art, mammalian expression systems will result in glycosylation, typically at highly conserved N-terminal sites in the Fc region. Stable clones may be verified for expression of an antibody specifically binding to human TIM-3. Positive clones may be expanded into serum-free culture medium for antibody production in bioreactors. Culture medium, into which an antibody has been secreted, may be purified by conventional techniques. For example, the medium may be conveniently applied to a Protein A or G Sepharose FF column that has been equilibrated with a compatible buffer. The column is washed to remove nonspecific binding components. The bound antibody is eluted, for example, by pH gradient and antibody fractions are detected, such as by SDS-PAGE, and then pooled. The antibody may be filtered and concentrated using common techniques. Soluble aggregate and multimers may be effectively removed by common techniques, including size exclusion or ion exchange. The product may be immediately frozen, for example at −70° C., or may be lyophilized.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. "Treatment," as it applies to a human, veterinary, or research subject, refers to therapeutic treatment, prophylactic or preventative measures, to research and diagnostic applications.

"Treat" means to administer a therapeutic agent, such as a composition containing any of the binding compounds of the present invention, internally or externally to a patient having one or more disease symptoms for which the agent has known therapeutic activity. Typically, the agent is administered in an effective amount to alleviate one or more disease symptoms in the patient or population to be treated, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every patient, it should alleviate the target disease symptom(s) in a statistically significant number of patients as determined by any statistical test known in the art such as the Student's t-test, the chi-square test, the U-test according to Mann and Whitney, the Kruskal-Wallis test (H-test), Jonckheere-Terpstra-test and the Wilcoxon-test.

"Conservative modifications" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitution in non-essential regions of a polypeptide does not substantially alter biological activity (see, e.g., Watson et al. (1987) Molecular Biology of the Gene, The Benjamin/Cummings Pub. Co., p. 224 (4th Ed.)). In addition, substitutions with structurally or functionally similar amino acids are less likely to disrupt biological activity.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health condition of the patient, the route and dose of administration and the severity of side effects. An effective amount can be the maximal dose or dosing protocol that avoids significant side effects or toxic effects.

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptide sequences. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions to be compared and ×100. For example, if 6 out of 10 positions in two sequences are matched or homologous when the sequences are optimally aligned, then the two sequences have 60% homology. Generally, the comparison is performed when two sequences are aligned to give maximum percent homology.

As used herein, the expressions "cell," "cell line," and "cell culture" are used interchangeably and all such designations include progeny. Thus, the words "transformants" and "transformed cells" include the primary subject cells and cultures derived therefrom regardless of the number of transfers. It should be also understood that all progeny may not be precisely identical in DNA content, due to deliberate or inadvertent mutations. Mutant progeny that have the same function or biological activity as screened in the originally transformed cells are included. Where distinct designations are intended, it will be clearly understood from the context.

As used herein, "polymerase chain reaction" or "PCR" refers to a procedure or technique in which minute amounts of a specific portion of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) Cold Spring Harbor Symp. Ouant. Biol. 51:263; Erlich, ed., (1989) PCR TECHNOLOGY (Stockton Press, N.Y.). The PCR test used in the present invention is considered to be one, but not the only, example of polymerase reaction method for amplifying a nucleic acid test sample. The method comprises the use of known nucleic acid sequences as primers and a nucleic acid polymerase to amplify or generate a specific portion of nucleic acid.

"Optional" or "optionally" means that the event or situation that follows may but does not necessarily occur, and the description includes the instances in which the event or circumstance does or does not occur. For example, "optionally contains 1-3 antibody heavy chain variable regions" means the antibody heavy chain variable region with specific sequence can be, but need not be, present.

"Pharmaceutical composition" refers to a mixture containing one or more compounds according to the present invention or a physiologically/pharmaceutically acceptable salt or produg thereof and other chemical components, such as physiologically/pharmaceutically acceptable carriers and excipients. The pharmaceutical composition aims at promoting the administration to an organism, facilitating the absorption of the active ingredient and thereby exerting a biological effect.

Furthermore, the present invention includes an agent for treating a disease related to TIM-3 positive cells, the agent comprises the monoclonal antibody or the antibody fragment thereof of the present invention as an active ingredient.

The disease related to the TIM-3 positive cells is not limited, so long as it is a disease related to the cell expressing TIM-3, such as cancer, autoimmune disease, and allergic disease.

The cancer includes blood cancer, breast cancer, uterine cancer, colorectal cancer, esophageal cancer, gastric cancer, ovarian cancer, lung cancer, renal cancer, rectal cancer, thyroid cancer, uterine cervix cancer, small intestinal cancer, prostate cancer and pancreatic cancer. Preferable examples of the cancer include blood cancer, esophageal cancer, gastric cancer, colorectal cancer, liver cancer and prostate cancer.

Examples of the blood cancer include acute myeloid leukemia (AML), chronic myeloid leukemia (CML), myelodysplastic syndromes (MDS), multiple myeloma, cutaneous T cell lymphoma (CTCL), peripheral T-cell lymphoma (PTCL), anaplastic large cell lymphoma (ALCL), acute lymphocytic leukemia (ALL), chronic lymphocytic leukemia (CLL), other lymphoid leukemia, NK cell lymphoma, Hodgkin lymphoma, non-Hodgkin's lymphoma such as Burkitt's lymphoma, and the like.

Specific examples of the autoimmune diseases include rheumatoid arthritis, psoriasis, Crohn's disease, Ankylosing spondylitis, multiple sclerosis, type I diabetes, hepatitis, myocarditis, Sjogren's syndrome, autoimmune hemolytic anemia after transplant rejection, blisters pemphigoid, Graves disease, Hashimoto's thyroiditis, systemic lupus erythematosus (SLE), myasthenia gravis, pemphigus, pernicious anemia, and the like.

Examples of the allergic diseases include acute or chronic reactive airway disease, bronchial asthma, atopic dermatitis, allergic rhinitis, urticaria, PIE syndrome, food allergies, hay fever, allergic nose, bronchial asthma, atopic dermatitis, anaphylactic shock and the like.

Further, the present invention relates to a method for immune assay or measurement of TIM-3, an agent for immune assay or measurement of TIM-3, a method for immune assay or measurement of cells expressing TIM-3, and a diagnostic agent for diagnosing a disease related to TIM-3 positive cells, comprising the monoclonal antibody or the antibody fragment of the present invention which specifically recognizes human TIM-3 and binds to the extracellular region or three-dimensional structure thereof as an active ingredient.

In the present invention, the method for detecting or measuring the amount of TIM-3 may be any known method. For example, it includes immune assay or measurement method.

The immune assay or measurement is a method in which the amount of antibody or antigen is detected or determined by using a labeled antigen or antibody. Examples of the immune assay or measurement method include radioactive substance-labeled immunoantibody method (RIA), enzyme immunoassay (EIA or ELISA), fluorescent immunoassay (FIA), luminescent immunoassay, Western blotting method, physicochemical method and the like.

The above diseases related to TIM-3 positive cells can be diagnosed by detecting or measuring cells expressing TIM-3 by using the monoclonal antibody or antibody fragment of the present invention.

For the detection of the cells expressing the polypeptide, known immunological detection methods can be used, and an immunoprecipitation method, a fluorescent cell staining method, an immune tissue staining method and the like are preferably used. Also, a fluorescent antibody staining method using FMAT 8100 HTS system (Applied Biosystem) and the like can be used.

In the present invention, the living sample to be used for detecting or measuring TIM-3 is not particularly limited, so long as it has a possibility of containing cells expressing TIM-3, such as tissue cells, blood, plasma, serum, pancreatic fluid, urine, fecal matter, tissue fluid or culture fluid.

The diagnostic agent containing the monoclonal antibody of the present invention or antibody fragment thereof, or conjugate thereof, may further contain a reagent for carrying out an antigen-antibody reaction or a reagent for detection of the reaction, depending on the desired diagnostic method. The reagent for carrying out the antigen-antibody reaction includes buffer, salt, and the like. The reagent for detection includes a reagent generally used for the immunological detection or measurement, such as a labeled secondary antibody which recognizes the monoclonal antibody, antibody fragment thereof or conjugates thereof, and a substrate corresponding to the labeling and the like.

EXAMPLES AND TEST EXAMPLES

Hereinafter, the present invention is further described with reference to examples. However, the scope of the present invention is not limited thereto. In the examples of the present invention, where specific conditions are not described, the experiments are generally conducted under conventional conditions as described in Antibody Technology Laboratory Manual and Molecular Cloning Manual of Cold Spring Harbor, or under conditions proposed by the material or product manufacturers. Where the source of the reagents is not specifically given, the reagents are commercially available conventional reagents.

Example 1

Preparation of TIM-3 Antigen and the Protein for Detection

1. Design and Expression of TIM-3 Antigen

UniProt Hepatitis A virus cellular receptor 2 (human HAVCR2, human TIM-3, Uniprot NO.: Q8TDQ0) was used as the template for TIM-3 of the present invention to design the amino acid sequence of antigens and the protein for detection. Alternatively, various tags were fused based on TIM-3 protein, cloned into pHr vector (produced in-house) or pTargeT vector (Promega, A1410) respectively, transiently expressed in 293 cells or stably expressed in CHO-S cells, and purified to obtain the antigen of the present invention and the proteins for detection. The TIM-3 antigens mentioned below all refer to the human TIM-3, unless specifically indicated.

TIM-3 extracellular domain and hIgG1 Fc fusion protein: TIM-3-Fc, for mice immunization.

(SEQ ID NO: 1)

MEFGLSWLFLVAILKGVQCSEVEYRAEVGQNAYLPCFYTPAAPGNLVPVC
WGKGACPVFECGNVVLRTDERDVNYWTSRYWLNGDFRKGDVSLTIENVTL
ADSGIYCCRIQIPGIMNDEKFNLKLVIKPAKVTPAPTRQRDFTAAFPRML
TTRGHGPAETQTLGSLPDINLTQISTLANELRDSRLANDLRDSGATIR*EP*
*KSSDKTHTCPPCPAPELLGGPSVFLFPPKPKDTLMISRTPEVTCVVVDVS*
*HEDPEVKFNWYVDGVEVHNAKTKPREEQYNSTYRVVSVLTVLHQDWLNGK*
*EYKCKVSNKALPAPIEKTISKAKGQPREPQVYTLPPSRDELTKNQVSLTC*
*LVKGFYPSDIAVEWESNGQPENNYKTTPPVLDSDGSFFLYSKLTVDKSRW*
*QQGNVFSCSVMHEALHNHYTQKSLSLSPGK*

NOTE:
Underlined portion represents a signal peptide;
Italic portion represents Fc.

Extracellular domain of TIM-3 with Flag and His tag: TIM-3-Flag-His, for detection.
TIM-3-Flag-His (SEQ ID NO: 2)

MEFGLSWLFLVAILKGVQCSEVEYRAEVGQNAYLPCFYTPAAPGNLVPVC
WGKGACPVFECGNVVLRTDERDVNYWTSRYWLNGDFRKGDVSLTIENVTL
ADSGIYCCRIQIPGIMNDEKFNLKLVIKPAKVTPAPTRQRDFTAAFPRML
TTRGHGPAETQTLGSLPDINLTQISTLANELRDSRLANDLRDSGATIRGS
*SDYKDDDDKHHHHHH*

NOTE:
Underlined portion represents a signal peptide;
Italic portion represents Flag-His tag.

-continued

Full length of TIM-3, for constructing TIM-3-overexpressed cell line
TIM-3-full length (SEQ ID NO: 3)

MFSHLPFDCVLLLLLLLLTRSSEVEYRAEVGQNAYLPCFYTPAAPGNLVP

VCWGKGACPVFECGNVVLRTDERDVNYWTSRYWLNGDFRKGDVSLTIENV

TLADSGIYCCRIQIPGIMNDEKFNLKLVIKPAKVTPAPTRQRDFTAAFPR

MLTTRGHGPAETQTLGSLPDINLTQISTLANELRDSRLANDLRDSGATI

RIGIYIGAGICAGLALALIFGALIFKWYSHSKEKIQNLSLISLANLPPSG

LANAVAEGIRSEENIYTIEENVYEVEEPNEYYCYVSSRQQPSQPLGCRFA

MP

NOTE:
signal peptide + extracellular region +
transmembrane region + Intracellular region 2. Purification of Recombinant TIM-3 Related Proteins, Hybridoma Antibody and Recombinant Antibody 2.1. Purification Steps for Recombinant TIM-3-Flag-His Protein:

The sample was centrifuged at high speed to remove impurities and concentrated to an appropriate volume. Ni-NTA affinity column (QIAGEN, Cat No. 30721) was equilibrated with PBS and washed with 2-5 column volumes. The supernatant without impurity was loaded on the column. The column was washed with PBS until the A280 reading returned to baseline. And then the column was washed with PBS to remove nonspecific hybridized proteins and the effluent was collected. Washing buffer (20 mM imidazole) and elution buffer (300 mM imidazole) was used successively, and the target protein was eluted and the elution peak was collected.

The collected eluent was further purified by ion exchange (HiLoad 16/600 Superdex 200 column). The column was equilibrated with 2-5 column volumes of PBS to ensure pH 7.4. The eluent buffer with target protein was concentrated and loaded on the column, the sample was collected. The obtained protein was identified by SDS-PAGE and LC-MS, and the correct sample was aliquoted for use.

2.2 Purification of Hybridoma, Recombinant Antibody and Fc Fusion Protein

A sample of expressed cell supernatant was centrifuged at high speed to remove impurities. The supernatant of hybridoma expression was purified by Protein G column, recombinant antibody and Fc fusion protein was purified by Protein A column. The column was washed with PBS until the A280 reading was reduced to baseline. The target protein was eluted with 100 mM sodium acetate (pH 3.0) and was neutralized with 1 M Tris-HCl (pH 8.0). The eluted sample was concentrated appropriately and then further purified by gel chromatography Superdex 200 (GE) which was equilibrated with PBS. The peak without aggregates was collected and aliquoted for use.

Example 2

Preparation of Anti-Human TIM-3 Monoclonal Antibody

1. Animal Immunization

The anti-human TIM-3 monoclonal antibody was produced by immunizing mice. Experimental SJL white mice, female, 6-8 week old (Beijing Weitong Lihua Experimental Animal Technology Co., Ltd., animal production license number: SCXK (Beijing) 2012-0001). Feeding environment was SPF level. After the mice were purchased, the animals were adapted in the laboratory for 1 week, with 12/12 hour light/dark cycle, at a temperature of 20-25° C. and humidity of 40-60%. The mice that had been adapted to the environment were immunized according to the schemes below. The antigen used for immunization was the extracellular domain of TIM-3 with Fc tag (SEQ ID NO:1).

Immunization scheme: mice were immunized with QuickAntibody-Mouse5W (KX0210041). The ratio of antigen to adjuvant was 1:1, 10 μg/mouse, once (first immunization/booster immunization). The antigen and adjuvant were mixed rapidly and thoroughly and then used for inoculation. The interval duration between the first and the second immunizations was 21 days, and after the second immunization, the interval duration was 14 days. The blood was collected from mice at 7 days after each immunization. The titers of the antibody in the mice serum were determined by the ELISA method. Mice with serum titers of antibody that were higher and tending to reach a plateau were selected for splenocyte fusion, a booster immunization was performed by 20 μg/mouse i.p. injection with antigens formulated in saline solutions three days before splenocyte fusion.

2. Splenocyte Fusion

Hybridoma cells were obtained by fusing splenic lymphocyte with myeloma Sp2/0 cells (ATCC® CRL-8287™) using an optimized PEG-mediated fusion procedure. The hybridoma cells were resuspended in complete medium (DMEM medium containing 20% FBS, 1×HAT and 1×OPI) with a density of 4-5E5/ml, and incubated in 96-well cell culture plates (100 μl/well), at 37° C., 5% $CO_2$ for 3-4 days. 100 μl/well HAT complete medium was added, and the incubation was continued for 3-4 days until forming needle-like clones. The supernatant was removed and 200 μl/well HAT complete medium (RPMI-1640 medium containing 20% FBS, 1×HT and 1×OPI) was added and cultivated at 37° C., 5% $CO_2$ for 3 days. Then the ELISA assay was performed.

3. Screening for Hybridoma Cells

Hybridoma culture supernatant was analyzed using ELISA method according to the cell growth density (see Example 4 and Test Example 4). Binding assay with TIM-3-over-expressed cells was performed by ELISA (see Example 4 and Test Example 2). The positive clones in both protein binding and cell binding assays were expanded immediately, frozen for cryopreservation, and sub-cloned two to three times to obtain a single-cell clone.

TIM-3 binding ELISA and cell binding assays were performed with each of the subcloned cells. Through the experiments described above, hybridoma clones were obtained, and mAb-1701 and mAb-1799 antibodies secreted by the hybridoma were obtained. The antibody was further produced by using serum-free culture, and purified according to the example of purification, for use in the test examples.

4. DNA Sequencing for Positive Hybridoma Clones

The procedure for cloning and sequencing the positive Hybridoma was as below: Hybridoma cells in logarithmic growth period were collected and RNA was extracted by Trizol according to the manual of the kit (Invitrogen, Cat No. 15596-018). Reverse transcription was performed by using the PrimeScript™ Reverse Transcriptase Kit (Takara, Cat No. 2680A). The cDNA obtained from reverse transcription was PCR amplified with mouse Ig-Primer Set (Novagen, TB326 Rev.B 0503) and sequenced by a sequencing company. The amino acid sequences of heavy chain and light chain variable regions of mAb-1799 and mAb-1701 were obtained as follows:

```
mAb-1701 heavy chain variable region
                                          (SEQ ID NO: 4)
EVQLQQSGELVKPGASVKISCKASGYTFTDYYMNWVKQSHGKSLEWIAD

IIPNNGGSKYNQKFKDKATLTVDKSSSTAYMELRSLTSEDSAVYYCATW

GYGSSYRWFDYWGQGTLVSVSA

mAb-1701 light chain variable region
                                          (SEQ ID NO: 5)
DIQMTQSPASQSASLGESVTITCLASQPIGIWLAWYQQKPGKSPQLLIY

AATSLADGVPSRFSGSGSGTKFSFKISSLQAEDFVSYYCQQLYSSPWTF

GGGTKLEIK

mAb-1799 heavy chain variable region
                                          (SEQ ID NO: 6)
EVKLVESEGGLVQPGSSMKLSCTASGFTFSDYYMAWVRQVPEKGLEWVA

NINYDGSSTYYLDSLKSRFIISRDNAKNILYLQMNSLKSDDTATYYCAR

DVGYYGGNYGFAYWGQGTLVTVSA

mAb-1799 light chain variable region
                                          (SEQ ID NO: 7)
DIQMTQSPASLSASVGETVTITCRASDNIYSYLAWYQQKQGKSPQLLVY

NAKTLAEGVPSRFSGSGSGTQFSLKINSLQPEDFGSYYCQQHYGSPLTF

GAGTKLELK
```

The CDR sequences of each antibody heavy chain and light chain are as shown in Table 1.

TABLE 1

CDR sequences of antibody heavy chain and light chain

| Antibody | Heavy chain | | Light chain | |
|---|---|---|---|---|
| 1701 | HCDR1 | DYYMN<br>SEQ ID NO: 8 | LCDR1 | LASQPIGIWLA<br>SEQ ID NO: 11 |
| | HCDR2 | DIIPNNGGSKYNQKFKD<br>SEQ ID NO: 9 | LCDR2 | AATSLAD<br>SEQ ID NO: 12 |
| | HCDR3 | WGYGSSYRWFDY<br>SEQ ID NO: 10 | LCDR3 | QQLYSSPWT<br>SEQ ID NO: 13 |
| 1799 | HCDR1 | DYYMA<br>SEQ ID NO: 14 | LCDR1 | RASDNIYSYLA<br>SEQ ID NO: 17 |
| | HCDR2 | NINYDGSSTYYLDSLKS<br>SEQ ID NO: 15 | LCDR2 | NAKTLAE<br>SEQ ID NO: 18 |
| | HCDR3 | DVGYYGGNYGFAY<br>SEQ ID NO: 16 | LCDR3 | QQHYGSPLT<br>SEQ ID NO: 19 |

Example 3

Humanization of Anti-Human TIM-3 Murine Hybridoma Monoclonal Antibodies

1. Humanization of Anti-TIM-3 Antibody mAb-1701

Compared with the IMGT human antibody heavy and light chain variable region gene database by MOE software, the heavy and light chain variable region germline genes with high homology to mAb-1701 were selected as templates, and the CDRs of the murine antibodies were grafted into the corresponding human source template to form a variable region sequence in the order of FR1-CDR1-FR2-CDR2-FR3-CDR3-FR4. The amino acid residues were identified and annotated by the Kabat numbering system.

1.1 Selection of Humanized Framework Sequences for Hybridoma Clone mAb-1701

The humanized template for murine antibody mAb-1701 light chain is IGKV1-33*01 and hjk4.1, the humanized template for heavy chain is IGHV1-18*01 and hjh4.1. The sequences of humanized variable region are as follows:

```
h1701VH-CDR graft
                                          (SEQ ID NO: 20)
QVQLVQSGAEVKKPGASVKVSCKASGYTFTDYYMNWVRQAPGQGLEWMG

DIIPNNGGSKYNQKFKDRVTMTTDTSTSTAYMELRSLRSDDTAVYYCAR

WGYGSSYRWFDYWGQGTLVTVSS

h1701VL-CDR graft
                                          (SEQ ID NO: 21)
DIQMTQSPSSLSASVGDRVTITCLASQPIGIWLAWYQQKPGKAPKLLIY

AATSLADGVPSRFSGSGSGTDFTFTISSLQPEDIATYYCQQLYSSPWTE

GGGTKVEIK
NOTE:
The order is FR1-CDR1-FR2-CDR2-FR3-CDR3-FR4,
italic sequence is FR sequence,
underlined sequence is CDR sequence.
```

1.2. Template Selection and Back-Mutation Design for h1701

The specific mutations are shown in Table 2.

TABLE 2

Template selection and back-mutation design for h1701

| h1701_VL | | h1701_VH | |
|---|---|---|---|
| h1701_VL.1 | Grafted | h1701_VH.1 | Grafted |
| h1701_VL.1A | A43S | h1701_VH.1A | M48I |
| | | h1701_VH.1B | R98T |
| | | h1701_VH.1C | M48I, R98T |
| | | h1701_VH.1D | M48I, R98T, R38K, D89E |
| | | h1701_VH.1E | M48I, R98T, G49A, V68A, M70L |
| | | h1701_VH.1F | M48I, R98T, G49A, V68A, M70L, R38K, D89E |

NOTE:
For example, A43S denotes a back mutation from A to S at position 43 according to Kabat numbering system. Grafted indicates that the murine antibody CDRs were implanted into human germline FR sequences.

TABLE 3

Combinations of heavy and light chain variable regions of h1701 humanized antibody

| | h1701_VL.1 | h1701_VL.1A |
|---|---|---|
| h1701_VH.1 | h1701-005 | h1701-006 |
| h1701_VH.1A | h1701-007 | h1701-008 |
| h1701_VH.1B | h1701-009 | h1701-010 |
| h1701_VH.1C | h1701-011 | h1701-012 |
| h1701_VH.1D | h1701-013 | h1701-014 |
| h1701_VH.1E | h1701-015 | h1701-016 |
| h1701_VH.1F | h1701-017 | h1701-018 |

NOTE:
This table shows various sequence combinations of different mutations. For example, h1701-007 indicates that two mutations (light chain h1701_VL.1A and heavy chain h1701_VH.1A) are present on the humanized murine antibody h1701-007. The others are similar.

The specific sequences for humanized antibody 1701 are as follows:

```
>h1701_VH.1
                    (the same as h1701VH-CDR graft, SEQ ID NO: 22)
QVQLVQSGAEVKKPGASVKVSCKASGYTFTDYYMNWVRQAPGQGLEWMGDII

PNNGGSKYNQKFKDRVTMTTDTSTSTAYMELRSLRSDDTAVYYCARWGYGSSY

RWFDYWGQGTLVTVSS

>h1701h1701_VH.1A
                                                      (SEQ ID NO: 23)
QVQLVQSGAEVKKPGASVKVSCKASGYTFTDYYMNWVRQAPGQGLEWIGDIIP

NNGGSKYNQKFKDRVTMTTDTSTSTAYMELRSLRSDDTAVYYCARWGYGSSYR

WFDYWGQGTLVTVSS

>h1701_VH.1B
                                                      (SEQ ID NO: 24)
QVQLVQSGAEVKKPGASVKVSCKASGYTFTDYYMNWVRQAPGQGLEWMGDII

PNNGGSKYNQKFKDRVTMTTDTSTSTAYMELRSLRSDDTAVYYCATWGYGSSY

RWFDYWGQGTLVTVSS

>h1701_VH.1C
                                                      (SEQ ID NO: 25)
QVQLVQSGAEVKKPGASVKVSCKASGYTFTDYYMNWVRQAPGQGLEWIGDIIP

NNGGSKYNQKFKDRVTMTTDTSTSTAYMELRSLRSDDTAVYYCATWGYGSSYR

WFDYWGQGTLVTVSS

>h1701_VH.1D
                                                      (SEQ ID NO: 26)
QVQLVQSGAEVKKPGASVKVSCKASGYTFTDYYMNWVKQAPGQGLEWIGDII

PNNGGSKYNQKFKDRVTMTTDTSTSTAYMELRSLRSEDTAVYYCATWGYGSSY

RWFDYWGQGTLVTVSS

>h1701_VH.1E
                                                      (SEQ ID NO: 27)
QVQLVQSGAEVKKPGASVKVSCKASGYTFTDYYMNWVRQAPGQGLEWIADIIP

NNGGSKYNQKFKDRATLTTDTSTSTAYMELRSLRSDDTAVYYCATWGYGSSYR

WFDYWGQGTLVTVSS

>h1701_VH.1F
                                                      (SEQ ID NO: 28)
QVQLVQSGAEVKKPGASVKVSCKASGYTFTDYYMNWVKQAPGQGLEWIADII

PNNGGSKYNQKFKDRATLTTDTSTSTAYMELRSLRSEDTAVYYCATWGYGSSYR

WFDYWGQGTLVTVSS

>h1701_VL.1
                   (identical to h1701VL-CDR graft, SEQ ID NO: 29)
DIQMTQSPSSLSASVGDRVTITCLASQPIGIWLAWYQQKPGKAPKLLIYAATSLA

DGVPSRFSGSGSGTDFTFTISSLQPEDIATYYCQQLYSSPWTFGGGTKVEIK

>h1701_VL.1A
                                       (identical to SEQ ID NO: 30)
DIQMTQSPSSLSASVGDRVTITCLASQPIGIWLAWYQQKPGKSPKLLIYAATSLAD

GVPSRFSGSGSGTDFTFTISSLQPEDIATYYCQQLYSSPWTFGGGTKVEIK
```

2. Humanization of Anti-TIM-3 Antibody mAb-1799

Compared with the IMGT human antibody heavy and light chain variable region gene database and MOE software, the heavy and light chain variable region germline genes with high homology to mAb-1799 were selected as templates. The CDRs of the murine antibodies were grafted into the corresponding human source template to form a variable region sequence in the order of FR1-CDR1-FR2-CDR2-FR3-CDR3-FR4. The amino acid residues were identified and annotated by the Kabat numbering system.

2.1. Selection of Humanized Framework Sequences for Hybridoma Clone 1799

The humanized template for murine antibody mAb-1799 light chain is IGKV1-39*01 and hjk2.1, and the humanized template for heavy chain is IGHV3-7*01 and hjh4.1. The sequences of humanized variable region are as follows:

h1799VH-CDR graft (SEQ ID NO: 31)

*EVQLVESGGGLVQPGGSLRLSCAASGFTFS*DYYMA*WVRQAPGKGLEWVA*

NINYDGSSTYYLDSLKS*RFTISRDNAKNSLYLQMNSLRAEDTAVYYCAR*

*DVGYYGGNYGFAYWGQGTLVTVSS* h1799VL-CDR graft (SEQ ID NO: 32)

*DIQMTQSPSSLSASVGDRVTITC*RASDNIYSYLA*WYQQKPGKAPKLLIY*

NAKTLAE*GVPSRFSGSGSGTDFTLTISSLQPEDFATYYC*QQHYGSPLT*F*

*GQGTKLEIK*

NOTE:

The order is FR1-CDR1-FR2-CDR2-FR3-CDR3-FR4, italic sequence is FR sequence, underlined sequence is CDR sequence.

2.2. Template Selection and Back-Mutation Design for Hybridoma Clone 1799, See Table 4 as Below:

TABLE 4

Template selection and back-mutation design for hybridoma clone h1799

| h1799_VL | | h1799_VH | |
|---|---|---|---|
| h1799_VL.1 | Grafted | h1799_VH.1 | Grafted |
| h1799_VL.1A | I48V | h1799_VH.1A | Q3K |
| h1799_VL.1B | I48V, K45Q | h1799_VH.1B | Q3K, R87K |
| h1799_VL.1C | I48V, K45Q, A43S | | |
| h1799_VL.1D | I48V, K45Q, A43S, T85S | | |

NOTE:
For example, I48V denotes a back mutation from I to V at position 48 according to Kabat numbering system. Grafted indicates that the murine antibody CDRs were implanted into human germline FR sequences.

TABLE 5

Combinations of heavy and light chain variable regions of humanized murine antibody 1799

| | h1799_VL.1 | h1799_VL.1A | h1799_VL.1B | h1799_VL.1C | h1799_VL.1D |
|---|---|---|---|---|---|
| h1799_VH.1 | h1799-005 | h1799-006 | h1799-007 | h1799-008 | h1799-009 |
| h1799_VH.1A | h1799-010 | h1799-011 | h1799-012 | h1799-013 | h1799-014 |
| h1799_VH.1B | h1799-015 | h1799-016 | h1799-017 | h1799-018 | h1799-019 |

NOTE:
This table shows various sequence combinations of different mutations. For example, h1799-005 indicates that two mutations (light chain h1799_VL.1A and heavy chain h1799_VH.1A) are present on the humanized murine antibody h1799-005. The others are similar.

The specific sequences of humanized 1799 are as follows:

```
>h1799_VH.1
                    (identical to h1799VH-CDR graft, SEQ ID NO: 33)
EVQLVESGGGLVQPGGSLRLSCAASGFTFSDYYMAWVRQAPGKGLEWVANINY

DGSSTYYLDSLKSRFTISRDNAKNSLYLQMNSLRAEDTAVYYCARDVGYYGGN

YGFAYWGQGTLVTVSS

>h1799_VH.1A
                                                    (SEQ ID NO: 34)
EVKLVESGGGLVQPGGSLRLSCAASGFTFSDYYMAWVRQAPGKGLEWVANINY

DGSSTYYLDSLKSRFTISRDNAKNSLYLQMNSLRAEDTAVYYCARDVGYYGGN

YGFAYWGQGTLVTVSS

>h1799_VH.1B
                                                    (SEQ ID NO: 35)
EVKLVESGGGLVQPGGSLRLSCAASGFTFSDYYMAWVRQAPGKGLEWVANINY

DGSSTYYLDSLKSRFTISRDNAKNSLYLQMNSLKAEDTAVYYCARDVGYYGGN

YGFAYWGQGTLVTVSS

>h1799_VL.1
                    (identical to h1799VL-CDR graft, SEQ ID NO: 36)
DIQMTQSPSSLSASVGDRVTITCRASDNIYSYLAWYQQKPGKAPKLLIYNAKTLA

EGVPSRFSGSGSGTDFTLTISSLQPEDFATYYCQQHYGSPLTFGQGTKLEIK

>h1799_VL.1A
                                                    (SEQ ID NO: 37)
DIQMTQSPSSLSASVGDRVTITCRASDNIYSYLAWYQQKPGKAPKLLVYNAKTL

AEGVPSRFSGSGSGTDFTLTISSLQPEDFATYYCQQHYGSPLTFGQGTKLEIK
```

-continued

```
>h1799_VL.1B
                                                  (SEQ ID NO: 38)
DIQMTQSPSSLSASVGDRVTITCRASDNIYSYLAWYQQKPGKAPQLLVYNAKTL

AEGVPSRFSGSGSGTDFTLTISSLQPEDFATYYCQQHYGSPLTFGQGTKLEIK

>h1799_VL.1C
                                                  (SEQ ID NO: 39)
DIQMTQSPSSLSASVGDRVTITCRASDNIYSYLAWYQQKPGKSPQLLVYNAKTL

AEGVPSRFSGSGSGTDFTLTISSLQPEDFATYYCQQHYGSPLTFGQGTKLEIK

>h1799_VL.1D
                                                  (SEQ ID NO: 40)
DIQMTQSPSSLSASVGDRVTITCRASDNIYSYLAWYQQKPGKSPQLLVYNAKTL

AEGVPSRFSGSGSGTDFTLTISSLQPEDFASYYCQQHYGSPLTFGQGTKLEIK
```

Example 4

Preparation and Test of Recombinant Chimeric Antibody and Humanized Antibody The combinations of human heavy chain IgG4/light chain kappa constant region and the various variable regions were selected for the antibody. S228P mutation was introduced into the Fc segment to increase the stability of the IgG4 antibody, and other mutations known in the field can also be used to increase the performance.

Sequences of heavy chain constant region are shown in SEQ ID NO: 41

```
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK
```

Sequences of light chain constant region are shown in SEQ ID NO: 42

```
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
```

1. Molecular Cloning of Chimeric Antibody Heavy Chain

Variable region gene sequences were obtained by sequencing the positive antibody molecules selected from hybridoma screening. The primers were designed according to the obtained sequences. The gene to be sequenced was used as a template to construct various antibody VH/VK gene fragments via PCR. The obtained fragments were inserted into expression vector pHr (with a signal peptide and hIgG4/hkappa constant region (CH1-FC/CL) fragment) via homologous recombination and a full-length expression plasmid of recombinant chimeric antibody VH-CH1-FC-pHr/VL-CL-pHr was constructed. Finally, the two chimeric antibodies, Ch1701 and Ch1799, were formed.

2. Molecular Cloning of Humanized Antibody

The designed sequences for humanized antibody were codon-optimized and coding sequences with human codon preference were obtained. The primers were designed, and various antibody VH/VK gene fragments were constructed. The obtained fragments were inserted into expression vector pHr (with a signal peptide and hIgG4/hkappa constant region (CH1-FC/CL) fragment) via homologous recombination and a full-length expression plasmid of a humanized antibody VH-CH1-FC-pHrNL-CL-pHr was constructed.

3. Expression and Purification of Recombinant Chimeric Antibody and Humanized Antibody The vectors expressing antibody heavy and light chains were transfected into HEK293E cells at the ratio of 1:1.2, and supernatant was collected after six days. The sample was centrifuged at high speed to remove impurities and purified by Protein A column. The column was washed with PBS until the A280 reading was reduced to baseline. The target protein was eluted with acidic elution buffer (pH 3.0-pH 3.5). 1 M Tris-HCl (pH 8.0-9.0) was used to neutralize the target protein. The eluted sample was concentrated appropriately and further purified by gel chromatography Superdex-200 (GE) which was equilibrated with PBS. The peak without aggregates was collected and aliquoted for use.

Example 5

Point Mutations of Antibody h1701

Deamidation is a common chemical modification which will influence the stability of antibody in later stage. Especially, it is generally to avoid high deamidation, oxidation or isomerization modification in CDR amino acids, or to decrease such modifications via mutations. According to the Accelerated Stability Test and Computer Simulation of Antibody structure and Hotspot Prediction, NNG site in heavy chain CDR2 of h1701 antibody is prone to deamidation. The above NNG is located in amino acid positions 54-56 in the antibody h1701 heavy chain variable region. According to the amino acid properties and Computer Simulation of Antibody structure, the amino acids of the above site can be replaced by any amino acid. Preferably, CDR2 variant of h1701 is: DIIP$X_1X_2X_3$GSKYNQKFKD (SEQ ID NO:43), wherein $X_1X_2X_3$ were amino acid residues at positions 54-56 in heavy chain variable region of h1701 antibody, $X_1$ is selected from Asn, Leu, Val, Met or Glu, $X_2$ is selected from Asn, Glu, Met, His, Lys, Leu, Ala or Val, $X_3$ is selected from Gly or Ala.

Furthermore, the CDR2 containing above mutations at positions 54-56 and the FR containing different back-mutations can form the following heavy chain variable region:

>h1701_VH.1-CDR2 mutant
(SEQ ID NO: 44)
QVQLVQSGAEVKKPGASVKVSCKASGYTFTDYYMNWVRQAPGQGLEWMGD
IIPX$_1$X$_2$X$_3$GSKYNQKFKDRVTMTTDTSTSTAYMELRSLRSDDTAVYYCAR
WGYGSSYRWFDYWGQGTLVTVSS >h1701_VH.1A-CDR2 mutant
(SEQ ID NO: 45)
QVQLVQSGAEVKKPGASVKVSCKASGYTFTDYYMNWVRQAPGQGLEWIGD
IIPX$_1$X$_2$X$_3$GSKYNQKFKDRVTMTTDTSTSTAYMELRSLRSDDTAVYYCAR
WGYGSSYRWFDYWGQGTLVTVSS >h1701_VH.1B-CDR2 mutant
(SEQ ID NO: 46)
QVQLVQSGAEVKKPGASVKVSCKASGYTFTDYYMNWVRQAPGQGLEWMGD
IIPX$_1$X$_2$X$_3$GSKYNQKFKDRVTMTTDTSTSTAYMELRSLRSDDTAVYYCAT
WGYGSSYRWFDYWGQGTLVTVSS >h1701_VH.1C-CDR2 mutant
(SEQ ID NO: 47)
QVQLVQSGAEVKKPGASVKVSCKASGYTFTDYYMNWVRQAPGQGLEWIGD
IIPX$_1$X$_2$X$_3$GSKYNQKFKDRVTMTTDTSTSTAYMELRSLRSDDTAVYYCAT
WGYGSSYRWFDYWGQGTLVTVSS -continued >h1701_VH.1D-CDR2 mutant
(SEQ ID NO: 48)
QVQLVQSGAEVKKPGASVKVSCKASGYTFTDYYMNWVKQAPGQGLEWIGD
IIPX$_1$X$_2$X$_3$GSKYNQKFKDRVTMTTDTSTSTAYMELRSLRSEDTAVYYCAT
WGYGSSYRWFDYWGQGTLVTVSS >h1701_VH.1E-CDR2 mutant
(SEQ ID NO: 49)
QVQLVQSGAEVKKPGASVKVSCKASGYTFTDYYMNWVRQAPGQGLEWIAD
IIPX$_1$X$_2$X$_3$GSKYNQKFKDRATLTTDTSTSTAYMELRSLRSDDTAVYYCAT
WGYGSSYRWFDYWGQGTLVTVSS >h1701_VH.1F-CDR2 mutant
(SEQ ID NO: 50)
QVQLVQSGAEVKKPGASVKVSCKASGYTFTDYYMNWVKQAPGQGLEWIAD
IIPX$_1$X$_2$X$_3$GSKYNQKFKDRATLTTDTSTSTAYMELRSLRSEDTAVYYCAT
WGYGSSYRWFDYWGQGTLVTVSS.

The exemplary sequences of antibody h1701 HCDR2 variants and humanized h1701_VH.1B-CDR2 variant containing the corresponding CDR2 variants (SEQ ID NO: 46) are shown in the following variants and in Table 6.

For example, the NNG in h1701-009 HCDR2 were designed as NLG, NVG, NNA, NMA, NEA, NHA, NMG, NEG, NKG, NAG, NHG (the sequences of the corresponding heavy chain variable region CDR2 are shown in SEQ ID NOs: 51-61). Construction of expression plasmid and expression of 293E were performed via molecular cloning. The affinity and stability of the mutated antibodies were further measured after purification.

The results of the affinity test of the exemplary variants are shown in test examples 1 and 3.

A series of specific amino acid mutations were made on h1701-009. These mutations include but not limited to those indicated in Table 6. The results of chemical stability tests are shown in the test example 9.

TABLE 6

Heavy chain variable region sequence of h1701-009 variants that prevent from deamidation

| Heavy chain variable regionVH | SEQ ID NO. for | the corresponding HCDR2 sequence |
|---|---|---|
| h1701-009 | SEQ ID NO: 24 | DIIPNNGGSKYNQKFKD (SEQ ID NO: 9) |
| h1701-009NLG | SEQ ID NO: 51 | DIIPNLGGSKYNQKFKD (SEQ ID NO: 62) |
| h1701-009NVG | SEQ ID NO: 52 | DIIPNVGGSKYNQKFKD (SEQ ID NO: 63) |
| h1701-009NNA | SEQ ID NO: 53 | DIIPNNAGSKYNQKFKD (SEQ ID NO: 64) |
| h1701-009NMA | SEQ ID NO: 54 | DIIPNMAGSKYNQKFKD (SEQ ID NO: 65) |
| h1701-009NEA | SEQ ID NO: 55 | DIIPNEAGSKYNQKFKD (SEQ ID NO: 66) |
| h1701-009NHA | SEQ ID NO: 56 | DIIPNHAGSKYNQKFKD (SEQ ID NO: 67) |
| h1701-009NMG | SEQ ID NO: 57 | DIIPNMGGSKYNQKFKD (SEQ ID NO: 68) |
| h1701-009NEG | SEQ ID NO: 58 | DIIPNEGGSKYNQKFKD (SEQ ID NO: 69) |
| h1701-009NKG | SEQ ID NO: 59 | DIIPNKGGSKYNQKFKD (SEQ ID NO: 70) |
| h1701-009NAG | SEQ ID NO: 60 | DIIPNAGGSKYNQKFKD (SEQ ID NO: 71) |
| h1701-009NHG | SEQ ID NO: 61 | DIIPNHGGSKYNQKFKD (SEQ ID NO: 72) |

The performance and benefits of the present antibodies are verified by test methods as indicated below.

Test Example 1

Binding Assay for Anti-TIM-3 Antibody to CHO-s Cells Overexpressing Human TIM-3

The binding activity of anti-TIM-3 antibody to CHO-S cells overexpressing human TIM-3 is detected via a binding assay. The TIM-3 full-length plasmid (produced in-house, SEQ ID NO: 3) was transfected into CHO-S cells by electroporation, the expression of TIM-3 was detected after two weeks of pressure selection. TIM-3-overexpressing cells were immobilized on a 96-well plate. After the addition of the antibody, signal strength was used to determine the binding activity of the antibody to Tim-3-overexpressing CHO-S cells. The particular procedures are as follows. AbTim-3 was used as a positive control, the sequence of which can be found in US20150218274A1 table 2 and was reproduced by our company.

The cells were inoculated on a 96-well plate with 4E5/ml density, 100 μg/well, and cultured overnight. Supernatant was discarded and the plate was washed three times with PBS. 100 μl/well of 4% PFA was added into each well, and the plate was fixed at room temperature for 30 minutes. The plate was washed three times with PBS. The liquid was discarded, and 200 μl of blocking solution (5% skim milk (Guangming skim milk powder) diluted with PBS) was added to each well. The plate was incubated at 37° C. for 2.5 h. Then the blocking solution was discarded, and the plate was washed 5 times with PBST buffer (pH 7.4 PBS containing 0.05% Tween-20). 50 μl/well of various concentrations of antibodies to be tested (antibody via hybridoma purification or humanized antibody), diluted with sample buffer, were added into each well, and incubated at 37° C. for 1 h. After incubation, the plate was washed 5 times with PBST buffer, 100 μl/well of HRP-labeled goat-anti-mouse secondary antibody (Jackson Immuno Research, Cat No. 115-035-003) or goat-anti-human secondary antibody (Jackson Immuno Research, Cat No. 109-035-003), diluted with sample dilution, was added into each well, and was incubated at 37° C. for 1 h. The plate was washed 6 times with PBST, and 100 μl/well TMB chromogenic substrates (KPL, Cat, No., 52-00-03) was added to each well. The plate was incubated at room temperature for 5-15 min. Reaction was stopped by the addition of 50 μl of 1 M $H_2SO_4$ to each well. The OD value at a wavelength of 450 nm was read on an ELISA microplate reader (BMG Labtech, NOVOStar) and EC50 value of the binding of TIM-3 antibody to Tim-3 over-expressing cells was calculated.

TABLE 7

EC50 of candidate antibodies from cell binding assays

| candidate antibody | Cell-based binding ELISA EC50(nM) |
|---|---|
| mAb-1701 | 0.122 |
| mAb-1799 | 0.117 |
| Ch1701 | 0.166 |
| h1701-005 | 0.602 |
| h1701-006 | 0.735 |
| h1701-007 | — |
| h1701-008 | 2.422 |
| h1701-009 | 0.187 |
| h1701-010 | 0.069 |
| h1701-011 | 0.188 |

TABLE 7-continued

EC50 of candidate antibodies from cell binding assays

| candidate antibody | Cell-based binding ELISA EC50(nM) |
|---|---|
| h1701-012 | 0.221 |
| h1701-013 | 0.199 |
| h1701-014 | 0.124 |
| h1701-015 | 0.265 |
| h1701-016 | 0.058 |
| h1701-017 | 0.105 |
| h1701-018 | 0.087 |
| Ch1799 | 0.080 |
| h1799-005 | 0.063 |
| h1799-006 | 0.095 |
| h1799-007 | 0.109 |
| h1799-008 | 0.067 |
| h1799-009 | 0.076 |
| h1799-010 | 0.077 |
| h1799-011 | 0.114 |
| h1799-012 | 0.158 |
| h1799-013 | 0.139 |
| h1799-014 | 0.116 |
| h1799-015 | 0.188 |
| h1799-016 | 0.117 |
| h1799-017 | 0.194 |
| h1799-018 | 0.215 |
| h1799-019 | 0.119 |

The results show that TIM-3 antibodies 1701 and 1799 and the humanized antibodies thereof have good binding activities to CHO-s cells expressing human full-length TIM-3 protein.

The binding activities to human TIM-3-overexpressing cells of h1701-009 and variants thereof having point mutations on HCDR2 are shown in Table 8.

TABLE 8

EC50 of candidate antibodies from cell-based binding assays

| candidate antibody | Binding ELISA EC50 (nM) |
|---|---|
| h1701-009 | 0.503 |
| h1701-009 NNA | 0.515 |
| h1701-009 NHA | 0.530 |
| h1701-009 NEA | 0.667 |
| h1701-009 NMA | 0.629 |
| h1701-009 NMG | 0.603 |
| h1701-009 NEG | 0.673 |
| h1701-009 NVG | 0.717 |
| h1701-009 NLG | 0.637 |
| h1701-009 NKG | 0.438 |
| h1701-009 NAG | 0.512 |
| h1701-009 NHG | 0.317 |

The results showed that variants of 1701-009 antibody having point mutations on HCDR2 have good binding activities to human TIM-3-overexpressing CHO-s cells.

Test Example 2

Competitive Test of Anti-TIM-3 Antibody

Antibody A was diluted to 2 μg/ml with PBS, pH 7.4 (Sigma, Cat No. P4417-100TAB) and 50 μg/well was added into 96-well microtiter plate (Corning, Cat No. CLS3590-100EA) and incubated at 37° C. for 2h. The liquid was discarded. 200 μl of blocking solution (5% skim milk (Guangming skim milk powder) diluted with PBS) was added to each well, and the plate was incubated at 37° C. for 2.5h or 4° C. overnight (16-18 hours). Then the blocking solution was discarded, the plate was washed 5 times with PBST buffer (PH 7.4 PBS containing 0.05% Tween-20). 50 μl/well of pre-mixture of 20 μg/ml and 4 μg/ml antibody B diluted with sample dilution (PH7.4 PBS containing 1% BSA) and 0.4 μg/ml biotin-labeled TIM-3-Fc protein (produced in-house, SEQ ID NO: 1) was added to each well. The plates was incubated at 37° C. for 1 h. After incubation, the liquid in microtiter plate was discarded, and the plate was washed 5 times with PBST buffer. 100 μl/well of HRP-labeled streptavidin (Sigma, Cat No. 52438) diluted with sample solution was added to each well, and the plate was incubated at 37° C. for 1 h. The plate was washed 5 times with PBST, 50 μl/well TMB chromogenic substrate (KPL, Cat, No., 52-00-03) was added to each well and the plate was incubated at room temperature for 5-10 min. The reaction was stopped by the addition of 50 μl/well 1M $H_2SO_4$ to each well. The OD value at wavelength of 450 nm was read on an ELISA microplate reader (BMG Labtech, NOVOStar) and competitive effects of different antibodies for binding to Tim-3 were calculated.

TABLE 9

Competitive test of mAb-1701 and mAb-1799 for binding to TIM-3

| | μg/ml | mAb-1701 | mAb-1799 |
|---|---|---|---|
| mAb-1701 | 20 | 0.054 | 1.599 |
| | 4 | 0.072 | 1.685 |
| mAb-1799 | 20 | 0.835 | 0.091 |
| | 4 | 0.86 | 0.077 |

The results showed that there was no competitive relationship between mAb-1701 and mAb-1799 in binding to TIM-3.

Test Example 3

Affinity Assay for TIM-3 Antibody by Using Biacore

1. Affinity Assay for Murine Antibody by Using Biacore System

According to the method described in the manual of the mouse antibody capture antibody Kit (Cat. #BR-1008-38, GE), mouse antibody capture antibody was covalently coupled to the biosensor chip CM5 (Cat. #BR-1000-12, GE), to capture the antibody to be tested. Then TIM-3-His antigen (Sino. Biol, Cat. 10390-H03H) was flowed through the surface of the chip. The reaction signal was detected in real-time using Biacore instrument to obtain the association and dissociation curves. Finally the affinity value was obtained by fitting. In the experiment, after each cycle of dissociation was finished, the biosensor chip was washed with the regenerative solution in the mouse capture antibody Kit. The results are shown in table 10.

TABLE 10

Affinity test for candidate antibody

| Candidate antibody | mobile phase | affinity (M) |
|---|---|---|
| h1701 | TIM-3-His | 1.82E−10 |
| h1799 | | 2.36E−10 |

The results show that TIM-3 antibody mAb-1701 and mAb-1799 have strong binding activity and affinity to human TIM-3 protein.

2. Affinity Assay for Chimeric Antibody and Humanized Antibody by Using Biacore System According to the method described in the manual of the human antibody capture Kit (Cat. #BR-1008-39, GE), human antibody captured antibody was covalently coupled to the biosensor chip CM5 (Cat. #BR-1000-12, GE), so as to affinity capture the antibody to be tested. Then TIM-3-Flag-His antigen (produced in-house, SEQ ID NO: 2) was flowed through the surface of the chip. The reaction signal was detected in real-time using Biacore instrument to obtain the association and dissociation curves. Finally, the affinity value was obtained by fitting, see Table 11 below. In the experiment, after each cycle of dissociation was finished, the biosensor chip was washed with the regenerative solution in the human capture antibody Kit.

TABLE 11

Affinity of anti-TIM-3 antibody

| candidate antibody | mobile phase | affinity (M) |
|---|---|---|
| Ch1701 | TIM-3-His | 1.39E−9 |
| h1701-009 | | 1.34E−9 |
| h1701-010 | | 2.25E−9 |
| h1701-016 | | 1.60E−9 |
| Ch1799 | | 1.76E−9 |
| h1799-005 | | 1.78E−9 |
| h1799-006 | | 1.89E−9 |
| h1799-010 | | 2.48E−9 |

The results show that the obtained humanized antibodies of the present invention have strong binding activities and affinities to human TIM-3 protein (not all of the results are shown).

The binding affinity of h1701-009 variant antibody having point mutations on HCDR2 was detected by using BIAcore. The results are shown in Table 12.

TABLE 12

Affinity of anti-TIM-3 antibody

| stationary phase | mobile phase | affinity (M) |
|---|---|---|
| h1701-009 | TIM-3-His | 5.99E−10 |
| h1701-009 NAG | | 5.79E−10 |
| h1701-009 NEG | | 6.40E−10 |
| h1701-009 NEA | | 6.53E−10 |
| h1701-009 NHG | | 6.40E−10 |
| h1701-009 NHA | | 5.97E−10 |
| h1701-009 NKG | | 4.72E−10 |
| h1701-009 NLG | | 6.40E−10 |
| h1701-009 NMG | | 6.75E−10 |
| h1701-009 NMA | | 6.53E−10 |
| h1701-009 NNA | | 5.69E−10 |
| h1701-009 NVG | | 5.81E−10 |

The results show that the above h1701-009 variants still have strong affinities to TIM-3. The mutations at the NNG site do not affect the binding affinity of antibody to antigen.

Test Example 4

Cellular Immune Function Assay In Vitro

We established 3 functional tests in vitro to study the effect of anti-TIM-3 antibody on activating T lymphocytes: Mixed Lymphocyte Reaction (MLR assay), PBMC Activation Test and Super antigen Staphylococcal Enterotoxin B (SEB) Stimulation Test.

1. Mixed Lymphocyte Reaction (MLR Assay)

The experimental procedures are described as follows:

1) Human peripheral blood mononuclear cells (PBMC) were collected and purified;

2) PBMCs were seeded in NUNC plate for 2 hours with a density of 2E6 cells/mL;

3) non-adherent cells were removed and adherent cells were stimulated for 5 days with GM-CSF (100 ng/mL) and IL-4 (100 ng/mL), and then incubated with TNFα (100 ng/mL) for 2 days to induce the maturation of DC cells;

4) The mature DC cells were mixed with PBMCs from different donors at a ratio of 1:5, cultured on 96-well plates, which were pre-coated with 10 ng/mL CD3 antibody, while different concentrations of h1701-009, h1799-005, AbTIM-3 and negative control Fc-IgG were added;

(5) the concentration of IFNγ in the supernatant was detected by ELISA after 5 days (results shown as in FIG. 2A to 2C).

The results show that h1701-009, h1799-005 and AbTIM-3 effectively stimulated the secretion of IFNγ; h1701-009 and h1799-005 showed stronger stimulating effects.

2. PBMC Activation Test

The experimental procedures are briefly described as follows:

1) Human peripheral blood mononuclear cells (PBMCs) were collected and purified, and 96-well plates were coated with CD3 and CD28 antibodies, both with concentrations of 10 ng/mL;

2) PBMCs were seeded on the coated 96-well plates with densities of 1E5 cells/well, and different concentrations of the TIM-3 antibodies and the negative control Fc-IgG were added at the same time;

3) After 6 days, the cells were collected for staining of the intracellular IFNγ and TIM-3. The proportion of IFNγ positive cells (IFNγ+%) (IFNγ Geo mean value in all cells) and the proportion of IFNγ and TIM-3 double positive cells (TIM-3+IFNγ+%) (IFNγ Geo mean value in TIM-3+cells) were analyzed by FACS (FIG. 3A to 3D).

The results show that h1701-009, h1799-005 and AbTIM-3 increased the percentage of IFNγ positive cells and the expression of IFNγ to different degrees, and the effects of h1701-009 and h1799-005 were stronger.

3. SEB Stimulation Test

The experimental procedures are described as follows:

1) Human peripheral blood mononuclear cells (PBMCs) were collected and purified;

2) PBMCs were seeded on the coated 96-well plates with a densitiy of 1E5 cells/well and 1 ng/mL SEB and different concentrations of the TIM-3 antibody and the negative control Fc-IgG were added at the same time;

3) After 5 days, the supernatant was collected and IL12 and IFNγ were detected by ELISA (see FIGS. 4A and 4B, respectively).

The results show that all of h1701-009, h1799-005 and AbTIM-3 effectively increased the secretion of IL12 and IFNγ induced by SEB, while h1701-009 and h1799-005 showed better performance at low doses.

Test Example 5

Pharmacokinetics (PK) Assay for Humanized Anti-TIM-3 Antibody, h1701-009, h1799-005 in Rats 12 SD rats, weighted 180-240 g, were purchased from Sippr-BK laboratory animal Co. Ltd. During the feeding period, the rats were given ad libitum access to water and diet. The duration of adaptation in the laboratory environment was not less than 3 days with the 12/12-hour light-dark cycles regulation (the temperature was 16-26° C., the relative humidity was 40-70%). One day before the experiment, SD rats were numbered and randomly divided into groups, 3 rats in each group (2 males and 1 females). On the day of the experiment, two groups of rats were intravenously injected with test drug h1701-009, at doses of 3 mg/kg and 10 mg/kg; two groups of rats were intravenously injected with test drug h1701-005, at doses of 3 mg/kg and 10 mg/kg. The volume of intravenous injection was 5 mL/kg.

Before administration and 5 min, 8 h, 1 d, 2 d, 4 d, 7 d, 10 d, 14 d, 21 d, 28 d post administration, blood was collected at each time point. 0.2 mL of whole blood was collected from each animal, without anticoagulant. The blood sample was placed at 4° C. for 30 min, and then centrifuged at 1000 g for 15 min. The supernatants were taken into an EP tube and stored at −80° C.

The concentrations of serum antibodies were measured by ELISA and the pharmacokinetic parameters were calculated by Winnolin software. See Table 13 for main pharmacokinetic parameters.

TABLE 13

Half-lives of h1799-005 and h1701-009 in rats

| | h1799-005 | | h1701-009 | |
|---|---|---|---|---|
| Dose (mg/kg) | 3 | 10 | 3 | 10 |
| $t_{1/2}$ (day) | 13.6 ± 1.1 | 11.4 ± 1.7 | 10.6 ± 1.8 | 15.5 ± 2.5 |

After SD rats were intravenously injected with anti-TIM-3 antibodies h1701-009 and h1799-005 at a dose of 10 mg/kg, the serum levels in rats were similar. With respect to antibody h1799-005, the increased serum levels at administration doses of 3 and 10 mg/kg were linearly correlated with the increase in the administration dose; whereas, with respect to antibody h1701-009, the increased serum levels at administration doses of 3 and 10 mg/kg were slightly higher than the increase in administration dose. The elimination half-lives of antibodies h1701-009 and g1799-005 were similar.

Test Example 6

Thermal Stabilities of Antibodies h1701-009 and h1799-005 by DSC

Thermal stabilities were compared under different buffer systems with different pH values. The exemplary buffer systems with different pH's were, for example, 10 mM PB (pH 7), 15 mM His (pH 6.0) and 10 mM Acetate (pH 5.2). The samples were dissolved in the corresponding buffers, and the concentrations were controlled at about 1 mg/ml. The detection was performed by MicroCal* VP-Capillary DSC (Malvern). Prior to test, each sample and blank buffer were degassed using a vacuum degassing device for 1~2 min. Each well of the plate was added with 400 μl sample or blank buffer (the loading quantity was 300 μl). Finally, two pairs of wells were added with 14% Decon 90 and ddH2O, respectively for washing. Then the plate was sealed with a plastic cover. Scanning was started from the temperature of 25° C. and ended at 100° C., and the scanning rate was 60° C./h. The results are shown in Table 14, indicating that both h1701-009 and h1799-005 show good thermal stabilities in several test systems.

TABLE 14

Thermal stabilities of antibodies h1701-009 and h1799-005 at different pH's

| Sample | Buffer | Tm-onset (° C.) | TM (° C.) |
|---|---|---|---|
| h1701-009 | pH 7.0 | 63.09 | 74.59 |
| | pH 6.0 | 59.1 | 77.24 |
| | pH 5.2 | 60.32 | 77.13 |
| h1799-005 | pH 7.0 | 62.99 | 76.63 |
| | pH 6.0 | 60.01 | 77.49 |
| | pH 5.2 | 60.2 | 77.69 |

Test Example 7

Monitoring the Purity Via SEC-HPLC and Observing Periodic Stability at Certain Concentrations Exemplary conditions tested include, for example, the concentration of the sample was controlled at about 50 mg/mL. The stabilities of different antibodies in PBS (pH 7.4) were compared under conditions such as repeated freeze-thaw for 5 times at −80° C. and storage at 4° C. and 40° C. for one month. The purity of the antibody was measured using Xbridge protein BEH SEC 200A (Waters) HPLC column. After one month, both h1701-009 and h1799-005 show good stabilities and the purities by SEC were not significantly changed at 40° C. for one month.

Test Example 8

Chemical Stabilities of the Antibodies

The chemical stabilities of the h1701-009, h1799-005 and h1701-009 variants shown in SEQ ID NOs:51-55 were measured.

500 μg of antibody to be tested was dissolved in 500 μl of PBS, pH 7.4, and put in a 40° C. water bath. Sampling was performed on days 0, 14 and 28 for the enzymatic hydrolysis assay. 100 μg of each sample taken at different time points was dissolved in 100 μl of 0.2 M His-HCl M Gua-HCl solution, pH 6.0. 3 μl of 0.1 g/mL DTT was added, and then the sample was put in a 50° C. water bath for 1 hour. Then the sample was ultra-filtrated two times with 0.02 M His-HCl (pH 6.0), and enzymatically digested overnight in a 37° C. water bath with 34 of 0.25 mg/mL trypsin.

LC-MS analysis was performed by Agilent 6530 Q-TOF. The results show that h1799-005 did not show obvious isomerization, oxidation, and deamidation modification under the accelerated condition of 40° C. for one month, indicating that the molecule has good chemical stability. h1701-009 did not show obvious oxidation and isomerization modification. However, a strong deamidation modification at N54N55G56 site was observed in h1701-009. We attempted to introduce a series of the amino acid mutations, including exemplary mutations such as NLG, NVG, NMA, NEA, NNA and the like. It was demonstrated that these mutations did not affect the biological activity by using the in vitro activity assay. After acceleration test, the mutations were analyzed by LC-MS and the results show that all these mutations can effectively reduce the deamidation modification. The ratios of deamidation modifications in different variants after acceleration test are shown in Table 15.

TABLE 15

Chemical stabilities of h1701-009 variants having mutations in CDR2

| | day 0 | Week 1 | Week 2 |
|---|---|---|---|
| h1701-009 | 11.16% | 17.55% | 34.62% |
| h1701-009NLG | 0 | 0 | 0 |
| h1701-009NVG | 0 | 0 | 0 |
| h1701-009NMA | 0 | 0 | 0 |
| h1701-009NEA | 0 | 0 | 0 |
| h1701-009NNA | 0 | 0 | 13.58% |

Although the invention has been described in detail with figures and specific embodiments for the purpose of a clear understanding, the description and embodiments should not be interpreted as limiting the scope of this invention. All public contents of literatures and patents cited in this application are expressly incorporated by reference in their entireties.

What is claimed is:

1. A TIM-3 antibody or antigen-binding fragment thereof which binds to an extracellular region of human TIM-3 antigen and is selected from any one of the monoclonal antibody or antigen-binding fragment thereof of the following (a) to (m):

(a) a monoclonal antibody or antigen-binding fragment thereof comprising antibody heavy chain variable region HCDR1-3 sequences as shown in SEQ ID NOs: 8, 9 and 10, respectively, and antibody light chain variable region LCDR1-3 sequences as shown in SEQ ID NOs: 11, 12 and 13, respectively;

(b) a monoclonal antibody or antigen-binding fragment thereof comprising antibody heavy chain variable region HCDR1-3 sequences as shown in SEQ ID NOs: 8, 62 and 10, respectively, and antibody light chain variable region LCDR1-3 sequences as shown in SEQ ID NOs: 11, 12 and 13, respectively;

(c) a monoclonal antibody or antigen-binding fragment thereof comprising antibody heavy chain variable region HCDR1-3 sequences as shown in SEQ ID NOs: 8, 63 and 10, respectively, and antibody light chain variable region LCDR1-3 sequences as shown in SEQ ID NOs: 11, 12 and 13, respectively;

(d) a monoclonal antibody or antigen-binding fragment thereof comprising antibody heavy chain variable region HCDR1-3 sequences as shown in SEQ ID NOs: 8, 64 and 10, respectively, and antibody light chain variable region LCDR1-3 sequences as shown in SEQ ID NOs: 11, 12 and 13, respectively;

(e) a monoclonal antibody or antigen-binding fragment thereof comprising antibody heavy chain variable region HCDR1-3 sequences as shown in SEQ ID NOs: 8, 65 and 10, respectively, and antibody light chain variable region LCDR1-3 sequences as shown in SEQ ID NOs: 11, 12 and 13, respectively;

(f) a monoclonal antibody or antigen-binding fragment thereof comprising antibody heavy chain variable region HCDR1-3 sequences as shown in SEQ ID NOs: 8, 66 and 10, respectively, and antibody light chain variable region LCDR1-3 sequences as shown in SEQ ID NOs: 11, 12 and 13, respectively;

(g) a monoclonal antibody or antigen-binding fragment thereof comprising antibody heavy chain variable region HCDR1-3 sequences as shown in SEQ ID NOs: 8, 67 and 10, respectively, and antibody light chain variable region LCDR1-3 sequences as shown in SEQ ID NOs: 11, 12 and 13, respectively;

(h) a monoclonal antibody or antigen-binding fragment thereof comprising antibody heavy chain variable region HCDR1-3 sequences as shown in SEQ ID NOs: 8, 68 and 10, respectively, and antibody light chain variable region LCDR1-3 sequences as shown in SEQ ID NOs: 11, 12 and 13, respectively;

(i) a monoclonal antibody or antigen-binding fragment thereof comprising antibody heavy chain variable region HCDR1-3 sequences as shown in SEQ ID NOs: 8, 69 and 10, respectively, and antibody light chain variable region LCDR1-3 sequences as shown in SEQ ID NOs: 11, 12 and 13, respectively;

(j) a monoclonal antibody or antigen-binding fragment thereof comprising antibody heavy chain variable region HCDR1-3 sequences as shown in SEQ ID NOs: 8, 70 and 10, respectively, and antibody light chain variable region LCDR1-3 sequences as shown in SEQ ID NOs: 11, 12 and 13, respectively;

(k) a monoclonal antibody or antigen-binding fragment thereof comprising antibody heavy chain variable region HCDR1-3 sequences as shown in SEQ ID NOs: 8, 71 and 10, respectively, and antibody light chain variable region LCDR1-3 sequences as shown in SEQ ID NOs: 11, 12 and 13, respectively;

(l) a monoclonal antibody or antigen-binding fragment thereof comprising antibody heavy chain variable region HCDR1-3 sequences as shown in SEQ ID NOs: 8, 72 and 10, respectively, and antibody light chain variable region LCDR1-3 sequences as shown in SEQ ID NOs: 11, 12 and 13, respectively; and (m) a monoclonal antibody or antigen-binding fragment thereof comprising antibody heavy chain variable region HCDR1-3 sequences as shown in SEQ ID NOs:

14, 15 and 16, respectively, and antibody light chain variable region LCDR1-3 sequences as shown in SEQ ID NOs: 17, 18 and 19, respectively.

2. The TIM-3 antibody or antigen-binding fragment thereof according to claim 1, wherein the monoclonal antibody is a recombinant antibody.

3. The TIM-3 antibody or antigen-binding fragment thereof according to claim 2, wherein the monoclonal antibody is selected from the group consisting of a murine antibody, a chimeric antibody, and a humanized antibody, or an antigen-binding fragment thereof.

4. The TIM-3 antibody or antigen-binding fragment thereof according to claim 3, wherein the monoclonal antibody is a humanized antibody.

5. The TIM-3 antibody or antigen-binding fragment thereof according to claim 4, wherein the humanized antibody comprises a heavy chain variable region as shown in SEQ ID NO: 20 or 31.

6. The TIM-3 antibody or antigen-binding fragment thereof according to claim 4, wherein the humanized antibody comprises a heavy chain variable region having one or more amino acid back-mutation(s) in the framework (FR) region of the heavy chain variable region sequence of SEQ ID NO: 20 or 31, wherein the back-mutation(s) is selected from the group consisting of D89E, R98T, G49A, M48I, M70L, R38K and V68A back-mutations in the heavy chain variable region sequence of SEQ ID NO: 20, or selected from Q3K and R87K back-mutations in the heavy chain variable region sequence of SEQ ID NO: 31.

7. The TIM-3 antibody or antigen-binding fragment thereof according to claim 6, wherein the humanized antibody comprises a heavy chain variable region sequence selected from the group consisting of SEQ ID NOs: 23-28 or comprises a heavy chain variable region sequence selected from the group consisting of SEQ ID NOs: 34-35.

8. The TIM-3 antibody or antigen-binding fragment thereof according to claim 4, wherein the humanized antibody comprises a light chain variable region as shown in SEQ ID NO: 21 or 32.

9. The TIM-3 antibody or antigen-binding fragment thereof according to claim 4, wherein the humanized antibody comprises a light chain variable region having one or more amino acid back-mutation(s) in the framework (FR) region of the light chain variable region sequence of SEQ ID NO: 21 or 32, wherein the back-mutation(s) is the A43S back-mutation in the light chain variable region sequence of SEQ ID NO: 21 or selected from the group consisting of Q3K, I48V, K45Q, A43S and T85S back-mutations in the light chain variable region sequence of SEQ ID NO: 32.

10. The TIM-3 antibody or antigen-binding fragment thereof according to claim 9, wherein the humanized antibody comprises a light chain variable region sequence of SEQ ID NO: 30 or comprises a light chain variable region sequence selected from the group consisting of SEQ ID NOs: 37-40.

11. The TIM-3 antibody or antigen-binding fragment thereof according to claim 4, wherein the humanized antibody comprises a heavy chain variable region sequence selected from the group consisting of SEQ ID NOs: 22-28 and a light chain variable region sequence selected from the group consisting of SEQ ID NOs: 29-30; or comprises a heavy chain variable region sequence selected from the group consisting of SEQ ID NOs: 33-35 and a light chain variable region sequence selected from the group consisting of SEQ ID NOs: 36-40.

12. The TIM-3 antibody or antigen-binding fragment thereof according to claim 4, wherein the humanized antibody comprises a heavy chain variable region sequence selected from the group consisting of SEQ ID NOs: 51-61 and a light chain variable region sequence selected from the group consisting of SEQ ID NOs: 29-30.

13. The TIM-3 antibody or antigen-binding fragment thereof according to claim 1, wherein the antibody is a full-length antibody, comprising a human antibody constant region comprising a human heavy chain constant region sequence as shown in SEQ ID NO: 41 and comprising a human light chain constant region sequence as shown in SEQ ID NO: 42.

14. A composition comprising a therapeutically effective amount of the TIM-3 antibody or antigen-binging fragment thereof according to claim 1 and one or more pharmaceutically acceptable carriers, diluents or excipients.

15. A method for detecting or measuring human TIM-3 or TIM-3 positive cells, wherein the method comprises contacting the antibody or antigen-binding fragment thereof according to claim 1 with the human TIM-3 or TIM-positive cells.

16. A method of activating T lymphocytes in a subject comprising administering to the subject the pharmaceutical composition according to claim 14.

17. A TIM-3 antibody which binds to an extracellular region of human TIM-3 antigen, wherein the antibody comprises a heavy chain variable region having the amino acid sequence of SEQ ID NO: 31 and a light chain variable region having the amino acid sequence of SEQ ID NO: 32, and a human heavy chain constant region having the amino acid sequence of SEQ ID NO: 41 and a human light chain constant region having the amino acid sequence of SEQ ID NO: 42.

18. The method according to claim 16, wherein the subject has a disease related to human TIM-3 positive cells, wherein the disease is selected from the group consisting of cancer, autoimmune disease and allergic disease.

* * * * *